(12) United States Patent
Sanbuichi

(10) Patent No.: US 8,740,810 B2
(45) Date of Patent: Jun. 3, 2014

(54) BIOPSY NEEDLE, SAMPLE EXTRACTING UNIT, BIOPSY APPARATUS, AND METHOD OF CONTROLLING BIOPSY NEEDLE

(75) Inventor: Masahito Sanbuichi, Ashigarakami-gun (JP)

(73) Assignee: FUJIFULM Corporation, Tokyo (JP)

( * ) Notice: Subject to any disclaimer, the term of this patent is extended or adjusted under 35 U.S.C. 154(b) by 50 days.

(21) Appl. No.: 13/293,620

(22) Filed: Nov. 10, 2011

(65) Prior Publication Data

US 2012/0123295 A1    May 17, 2012

(30) Foreign Application Priority Data

Nov. 12, 2010  (JP) .................................. 2010-253659

(51) Int. Cl.
*A61B 10/00*     (2006.01)

(52) U.S. Cl.
USPC ............................................................. 600/566

(58) Field of Classification Search
USPC ................... 600/562–567; 604/22; 606/171
See application file for complete search history.

(56) References Cited

U.S. PATENT DOCUMENTS

| | | | | |
|---|---|---|---|---|
| RE33,258 E | * | 7/1990 | Onik et al. ....................... 604/22 |
| 7,179,232 B2 | * | 2/2007 | Sutton et al. ................. 600/567 |
| 8,075,495 B2 | | 12/2011 | Andreyko et al. |
| 8,282,573 B2 | | 10/2012 | Shabaz et al. |
| 2006/0200040 A1 | | 9/2006 | Weikel et al. |
| 2006/0200041 A1 | | 9/2006 | Weikel et al. |
| 2009/0270760 A1 | | 10/2009 | Leimbach et al. |

FOREIGN PATENT DOCUMENTS

| | | |
|---|---|---|
| EP | 2 113 204 A2 | 11/2009 |
| JP | 2006239433 A | 9/2006 |
| JP | 2006239434 A | 9/2006 |
| JP | 2007-520253 A | 7/2007 |
| JP | 2008508942 A | 3/2008 |
| JP | 2009261946 A | 11/2009 |
| JP | 2010000353 A | 1/2010 |
| JP | 2010221024 A | 10/2010 |

\* cited by examiner

*Primary Examiner* — Brian Szmal
(74) *Attorney, Agent, or Firm* — Sughrue Mion, PLLC

(57) ABSTRACT

The present invention relates to a biopsy needle, a sample extracting unit, a biopsy apparatus, and a biopsy needle control method. The biopsy needle includes an outer tube and an inner tube movably disposed within the outer tube. The inner tube has a plurality of inner openings defined in a side wall thereof. The outer tube has at least one outer opening defined in a side wall thereof. In response to movement of the inner tube, the outer opening selectively overlaps one of the inner openings thereby to define a communication port which communicates with an interior of the inner tube. The biopsy needle is incorporated in the sample extracting unit and the biopsy apparatus, and is controlled by the biopsy control method.

14 Claims, 21 Drawing Sheets

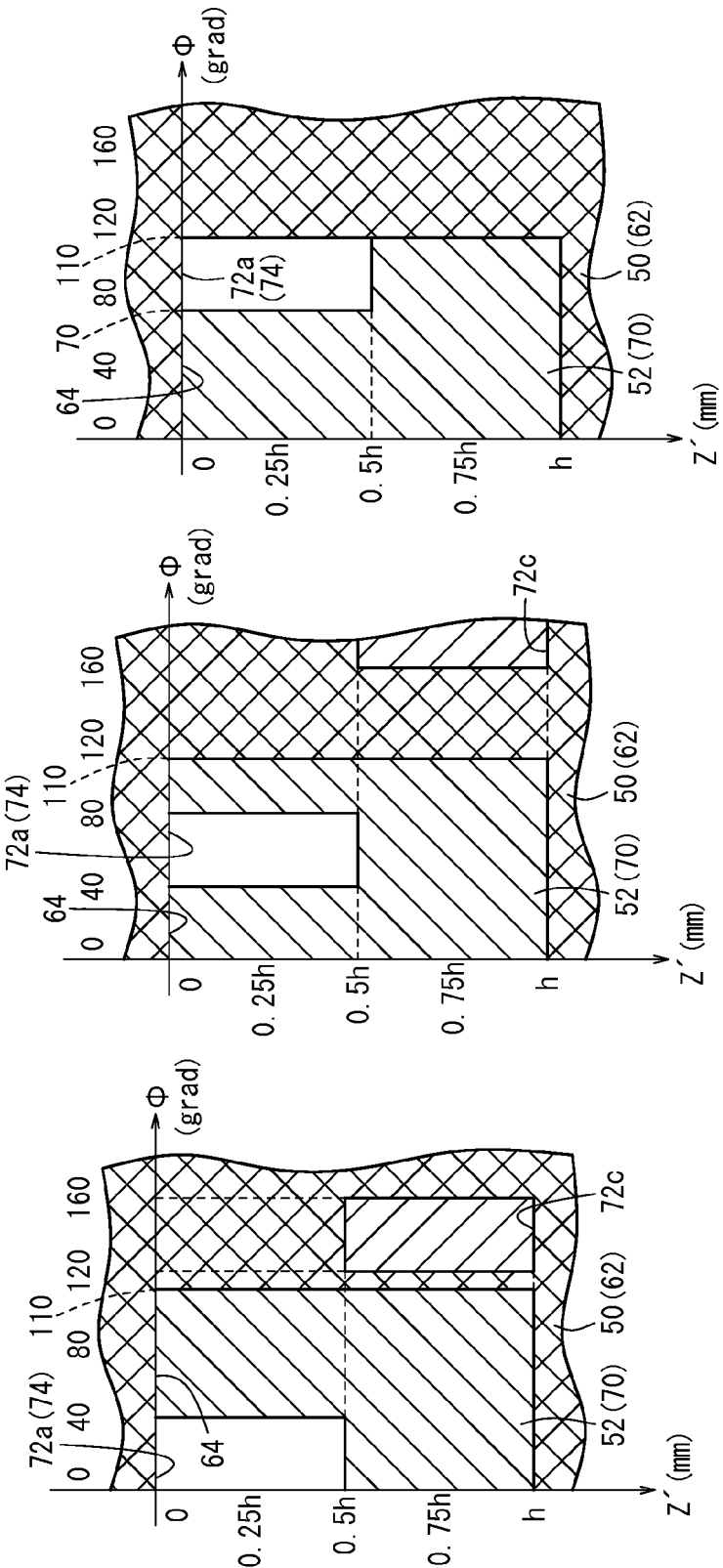

BIOPSY NEEDLE, SAMPLE EXTRACTING UNIT, BIOPSY APPARATUS, AND METHOD OF CONTROLLING BIOPSY NEEDLE

CROSS-REFERENCE TO RELATED APPLICATION

This application is based upon and claims the benefit of priority from Japanese Patent Application No. 2010-253659 filed on Nov. 12, 2010, of which the contents are incorporated herein by reference.

BACKGROUND OF THE INVENTION

1. Field of the Invention

The present invention relates to a biopsy needle for extracting a tissue sample from a biopsy region in an object to be examined, a sample extracting unit and a biopsy apparatus incorporating such a biopsy needle, and a method of controlling such a biopsy needle.

2. Description of the Related Art

Heretofore, doctors have widely performed a biopsy procedure for inserting a biopsy needle into an object to be examined, e.g., a living body such as a human body, and extracting a tissue sample from a biopsy region in the object. Generally, in order to reduce the physical burden on the object, it is desirable to insert the biopsy needle at an appropriate position for reliably and accurately extracting a tissue sample from the biopsy region. Accordingly, it has been customary in biopsy to carry out a stereoscopic image capturing process in which a radiation is applied to an object to be examined, and a stereoscopic image of the object is acquired, and then to calculate a three-dimensional position of the biopsy region from the stereoscopic image, before the biopsy procedure.

However, even if the three-dimensional position of the biopsy region is accurately grasped, in the case where the biopsy needle is inserted into the object, the needle may deviate from the desired puncture path for some reasons, e.g., an interference with a blood vessel in the object. As a result, the inserted biopsy needle does not follow the desired puncture path, and then the positional relationship, i.e., distance and direction relationship, between the biopsy region from which a tissue sample is to be extracted and the opening of the biopsy needle may deviate from an expected value. To solve the problem, there have been proposed various technologies for aspirating and sampling an appropriate amount of tissue from a biopsy region through a biopsy needle without the need for inserting the biopsy needle again.

Japanese Laid-Open Patent Publication No. 2007-520253 (PCT) discloses a bone marrow sampling apparatus having a double-tube structure which includes an outer tube having a plurality of aspiration holes defined therein and an inner tube having at least one hole defined therein. The bone marrow sampling apparatus is capable of adjusting the flow rate of a spinal fluid flowing through the double-tube structure by selectively moving the outer and inner tubes relatively to each other, or specifically translating and/or rotating the inner tube with respect to the outer tube. For example, the flow rate of the spinal fluid is adjusted by increasing or reducing the number of aspiration holes.

SUMMARY OF THE INVENTION

If a breast is an object to be examined in a biopsy, then a biopsy region (sample) is a semi-solid mass which chiefly contains fat. Such a semi-solid mass is less flowable, but more recoverable or elastic, than a bone marrow or the like.

If the bone marrow sampling apparatus disclosed in Japanese Laid-Open Patent Publication No. 2007-520253 (PCT) is used to aspirate a tissue sample from a breast through the aspiration holes, then since the bone marrow sampling apparatus tends to aspirate and sample a tissue from the biopsy region and also a tissue from other regions different from the biopsy region, the physical burden on the object increases disadvantageously.

The opening area of the aspiration holes may be increased and the aspirating pressure may be increased to enlarge an aspiration range, so that there is no need to insert the needle structure again. In this case, since the bone marrow sampling apparatus aspirates and samples a tissue from the wide aspiration range which includes not only the biopsy region but also a neighboring region, the physical burden on the object accordingly increases.

It is an object of the present invention to provide a biopsy needle, a sample extracting unit, a biopsy apparatus, and a method of controlling a biopsy needle which are capable of extracting a semi-solid tissue sample from a biopsy region even in a case where the biopsy needle is inserted at a position spaced from the biopsy region, without the need for inserting the biopsy needle again, and of minimizing the amount of the extracted tissue sample.

According to the present invention, there is provided a biopsy needle comprising an outer tube having a hollow cylindrical shape, and an inner tube having a hollow cylindrical shape and which is movably disposed within the outer tube for movement in an axial direction or a circumferential direction, wherein the inner tube has a plurality of inner openings defined in a side wall thereof, and the outer tube has at least one outer opening defined in an side wall thereof, and in response to movement of the inner tube, the at least one outer opening selectively overlaps one of the inner openings thereby to define a communication port which communicates with an interior of the inner tube.

As described above, the outer tube has at least one outer opening defined in a side wall thereof, and in response to movement of the inner tube, the at least one outer opening selectively overlaps one of the inner openings thereby to define a communication port which communicates with an interior of the inner tube. Thus, the range, i.e., the position and size, of the communication port can be set with increased freedom. Therefore, access of the biopsy needle to a biopsy region of an object to be examined can be optimized, and then the biopsy needle can extract a tissue sample without the need for subsequent re-insertion into the object even if the biopsy needle has been inserted into the object at a position spaced from the biopsy region. Since the outer tube and the inner tube jointly define the single communication port, the biopsy needle has only one aspirating range or sample extracting range for the biopsy region. Therefore, the biopsy needle avoids the aspiration and extraction of living body regions other than the biopsy region to be extracted, and hence minimizes the amount of a tissue sample extracted from the biopsy region.

The outer opening defined in the side wall of the outer tube should preferably comprise a single outer opening. The side wall of the inner tube is exposed to the exterior of the outer tube through only one place, i.e., the outer opening. Consequently, the entry of a liquid substance between the outer tube and the inner tube can be prevented.

The inner openings should preferably be disposed so as not to overlap each other in the axial direction of the inner tube. It is thus easy to perform a structural designing process for forming the single communication port.

The inner openings should preferably be disposed in respective positions which are different from each other in the axial direction of the inner tube. The position of the communication port in the axial direction can thus be changed freely.

The inner openings should preferably have respective opening areas which are different from each other and have respective centers of gravity disposed on one circumferential line. Owing thereto, the length of the communication port in the axial directions can be changed while the position of the peak of an aspirating pressure distribution being kept substantially in a given position. Therefore, an aspirating condition can be set with increased freedom.

The inner openings should preferably have respective opening areas which are identical to each other. The position of the communication port can thus be changed to any of various positions while the profile of an aspirating pressure distribution being kept substantially constant. Therefore, an aspirating condition can be set with increased freedom.

According to the present invention, there is also provided a sample extracting unit comprising a biopsy needle described above, and an aspirating mechanism for aspirating a mass which is disposed near the communication port defined by the outer tube and the inner tube, into the inner tube.

The aspirating mechanism should preferably have a changeable aspirating pressure. Consequently, an accurate aspiration control process can be carried out based on a combination of the range, i.e., position and size, of the communication port and the aspirating pressure.

The sample extracting unit should preferably further comprise a positional information input section for inputting positional information of the biopsy needle and the mass, and an aspirating pressure determiner for determining an aspirating pressure for the aspirating mechanism based on the positional information input by the positional information input section.

The sample extracting unit should preferably further comprise an opening information recorder for recording opening information about the outer opening and the inner openings, and an inner tube movement distance determiner for determining a movement distance of the inner tube based on the positional information input by the positional information input section and the opening information recorded by the opening information recorder.

According to the present invention, there is also provided a biopsy apparatus comprising a sample extracting unit described above, a radiation source for applying a radiation to an object to be examined of a subject, a radiation detector for detecting the radiation which has passed through the object and converting the detected radiation into a radiographic image, and a position calculator for calculating a three-dimensional position of a biopsy region in the object based on two radiographic images which are generated by the radiation detector in an image capturing process which is performed by applying the radiation from at least two angular positions to the object with the radiation source.

According to the present invention, there is further provided a method of controlling a biopsy needle, comprising the steps of inserting a biopsy needle described above into an object to be examined, and successively repeating at least once a first process for moving the inner tube of the biopsy needle and a second process for aspirating a mass which is disposed near the communication port defined by the outer tube and the inner tube, into the inner tube.

With the biopsy needle, the sample extracting unit, the biopsy apparatus, and the method of controlling a biopsy needle according to the present invention, the outer tube has at least one outer opening defined in an side wall thereof, and in response to movement of the inner tube having the inner openings, the at least one outer opening selectively overlaps one of the inner openings thereby to define a communication port which communicates with an interior of the inner tube. Owing thereto, the range, i.e., the position and size, of the communication port can be set with increased freedom. Therefore, access of the biopsy needle to a biopsy region of an object to be examined can be optimized, and the biopsy needle can extract a tissue sample without the need for subsequent re-insertion into the object even if the biopsy needle has been inserted into the object at a position spaced from the biopsy region. Since the outer tube and the inner tube jointly define the single communication port, the biopsy needle has only one aspirating range or sample extracting range for the biopsy region. Therefore, the biopsy needle can avoid the aspiration and extraction of living body regions other than the biopsy region to be extracted, and hence can minimize the amount of a tissue sample extracted from the biopsy region.

The above and other objects, features, and advantages of the present invention will become more apparent from the following description when taken in conjunction with the accompanying drawings in which preferred embodiments of the present invention are shown by way of illustrative example.

BRIEF DESCRIPTION OF THE DRAWINGS

FIGS. 7A through 7C are fragmentary developed side elevational views showing relative positional relationships between the side wall of the inner tube which has been turned through given angles and a side wall of an outer tube;

DESCRIPTION OF THE PREFERRED EMBODIMENTS

Figure 1:
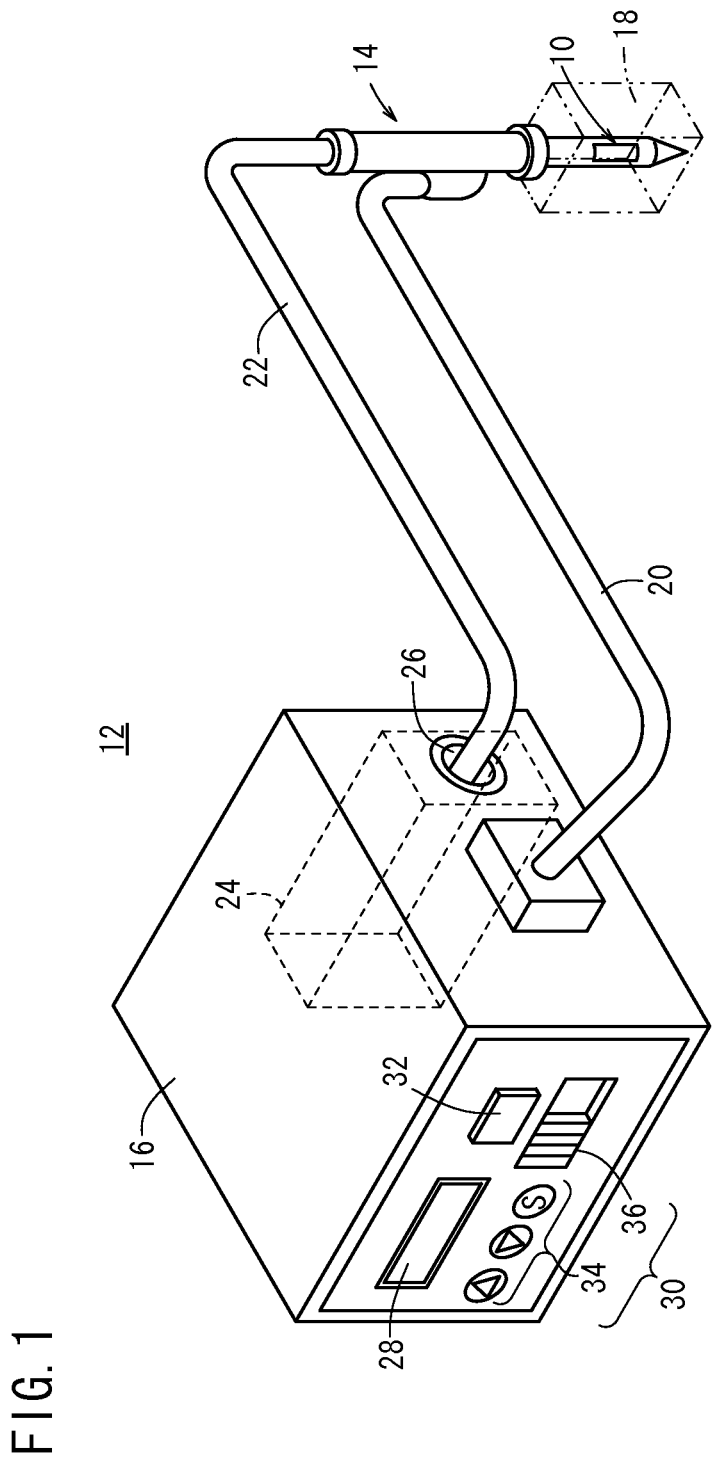
FIG. 1 is a perspective view of a sample extracting unit which incorporates a biopsy needle according to an embodiment of the present invention.

Biopsy needles according to preferred embodiments of the present invention in relation to a sample extracting unit and a biopsy apparatus incorporating the biopsy needle will be described in detail below with reference to the accompanying drawings.

Like or corresponding parts are denoted by like or corresponding reference characters throughout views.

FIG. 1 is a perspective view of a sample extracting unit 12 which incorporates a biopsy needle 10 according to an embodiment of the present invention.

As shown in FIG. 1, the sample extracting unit 12 basically includes a probe 14 having the biopsy needle 10 and a main unit body 16 for enabling the probe 14 to aspirate a tissue sample from an object 18 to be examined. In FIG. 1, the biopsy needle 10 is shown as being inserted in the object 18.

The probe 14, which is of a substantially hollow cylindrical shape, is electrically connected to the main unit body 16 by a cable 20. The probe 14 is also connected to the main unit body 16 by a flexible aspiration tube 22.

The main unit body 16, which is in the form of a rectangular parallelepiped, houses therein an aspirator (aspirating mechanism) 24 which is illustrated by the broken lines. The aspirator 24 has a compressor for generating compressed air to develop an aspirating pressure and is capable of changing the aspiration pressure. The aspirator 24 draws in a fluid through the aspiration tube 22 which is coupled to the aspirator 24 through an opening 26 that is defined in a side wall of the main unit body 16. The compressor of the aspirator 24 may be a turbocharger compressor which is of the axial flow type or the centrifugal type or a volumetric compressor which is of the reciprocating type or the rotary type.

The main unit body 16 includes another side wall having a display window 28, an operating section 30, and a switch 32.

The display window 28 displays various characters, figures, and/or symbols. For example, the display window 28 displays an aspirating pressure (setting value) of the aspirator 24. The display window 28 may display various setting values acquired from the probe 14 that is connected to the main unit body 16.

By pressing the switch 32, the aspirator 24 is instructed to start or end an aspiration process.

The operating section 30 includes a condition setting part 34 and a mode switcher 36. The condition setting part 34, which includes a plurality of buttons, can change the aspirating pressure (setting value) of the aspirator 24. The condition setting part 34 may set various operating conditions of the probe 14 that is connected to the main unit body 16.

The mode switcher 36 switches between different modes for setting an aspirating pressure of the aspirator 24. For example, the mode switcher 36 can switch between an automatic mode in which an aspirating pressure of the aspirator 24 is automatically set in response to a control signal from an external device, not shown, and a manual mode in which an aspirating pressure of the aspirator 24 is manually set by a user, who is typically a doctor or radiological technician handling the sample extracting unit 12, using the condition setting part 34.

Structural details of the probe 14 shown in FIG. 1 will be described below with reference to FIGS. 2 through 5.

Figure 2:
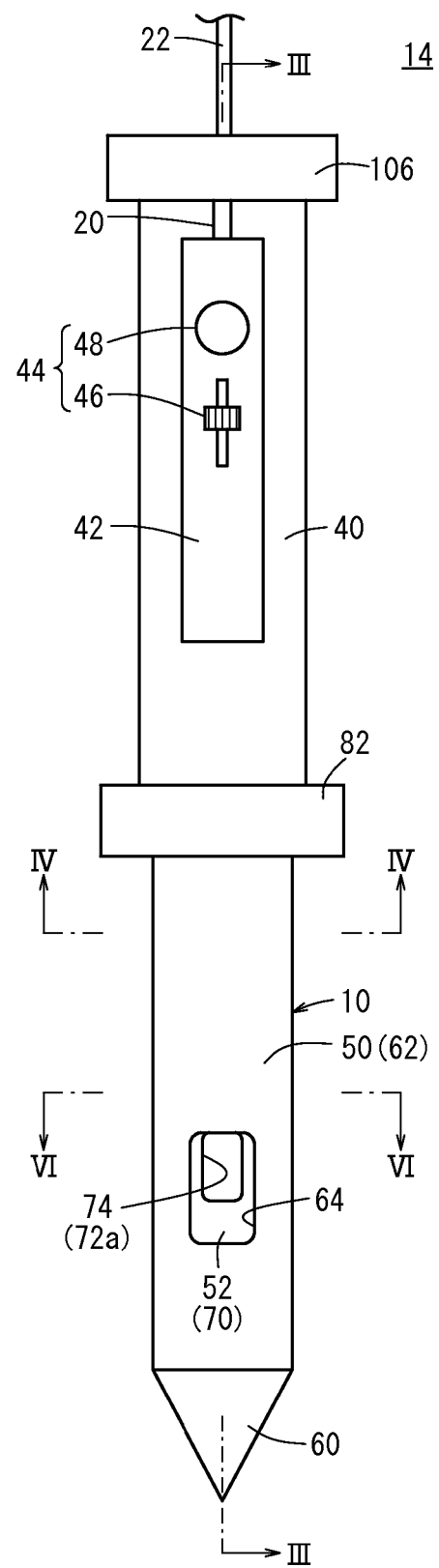
FIG. 2 is an enlarged front elevational view of a probe of the sample extracting unit shown in FIG. 1.
Figure 3:
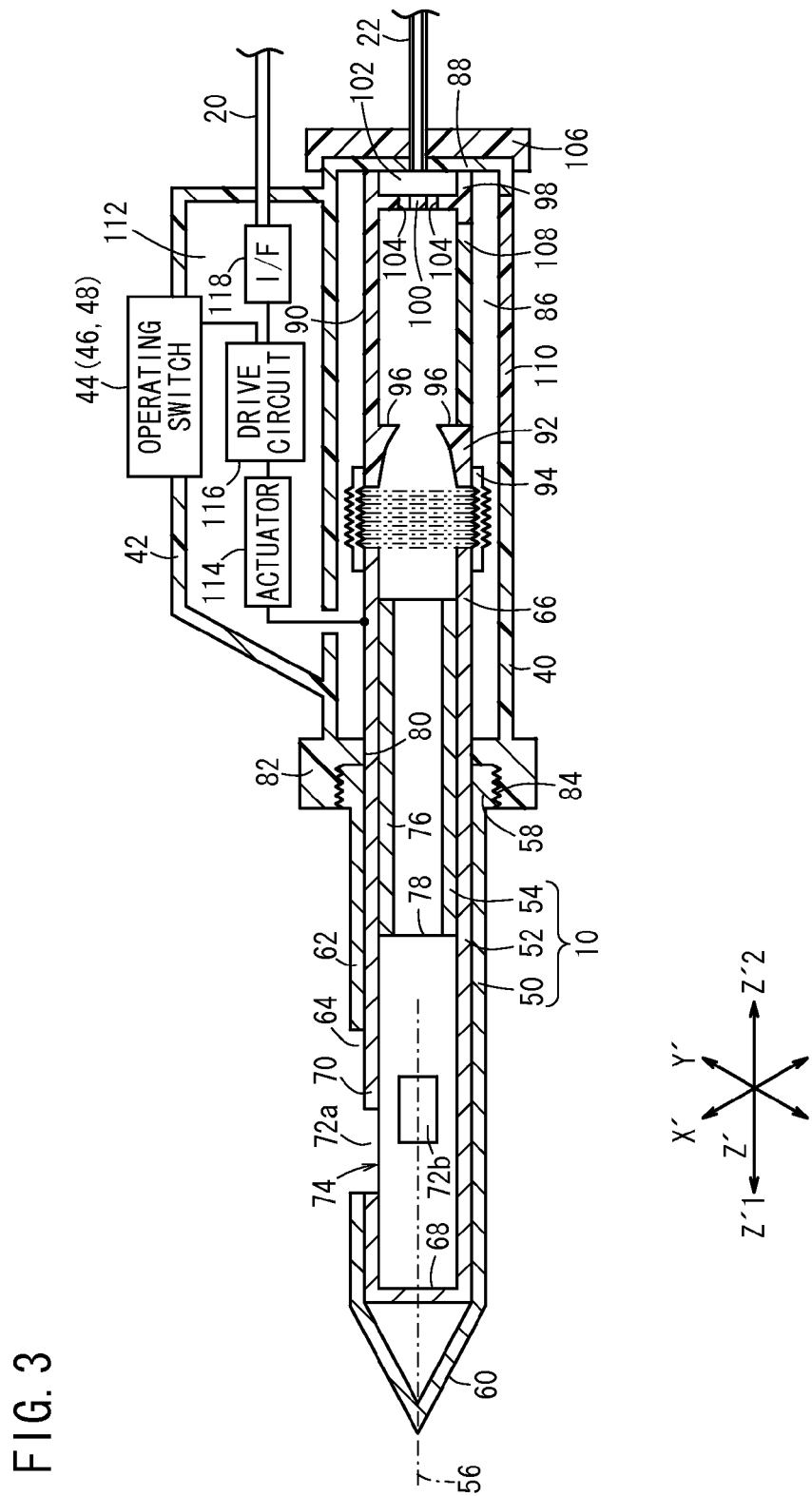
FIG. 3 is a cross-sectional view of the probe taken along line III-III of FIG. 2.
Figure 4:
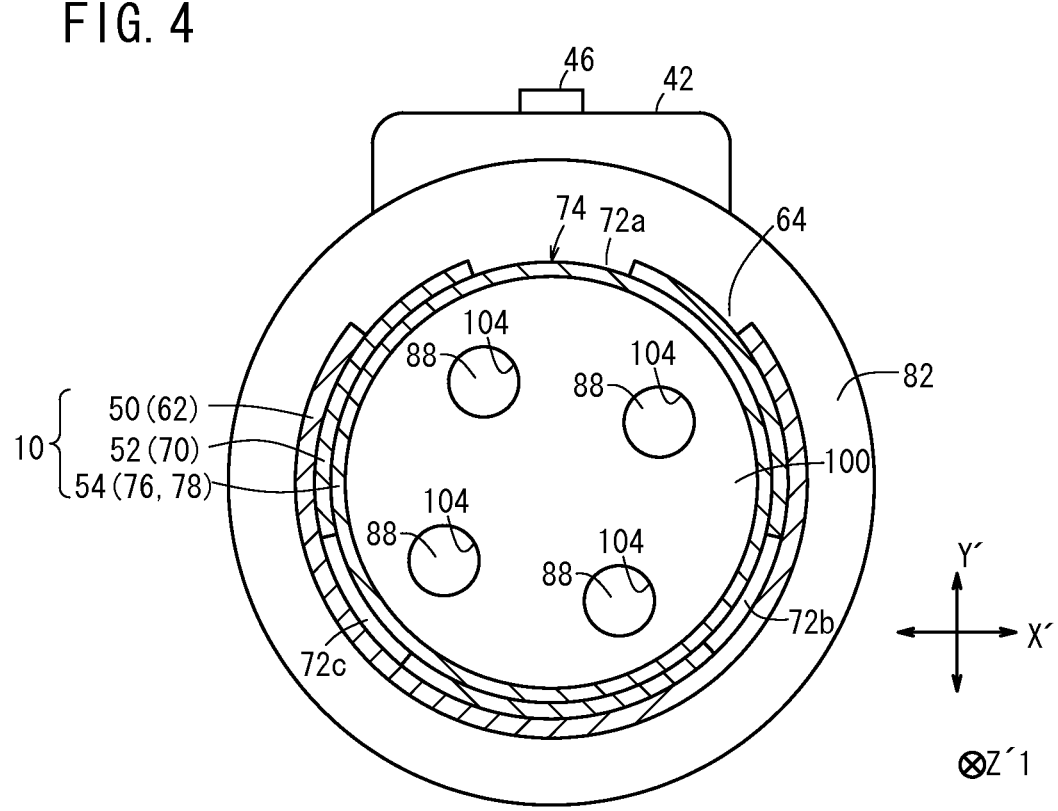
FIG. 4 is a cross-sectional view of the probe taken along line IV-IV of FIG. 2.
Figure 5:
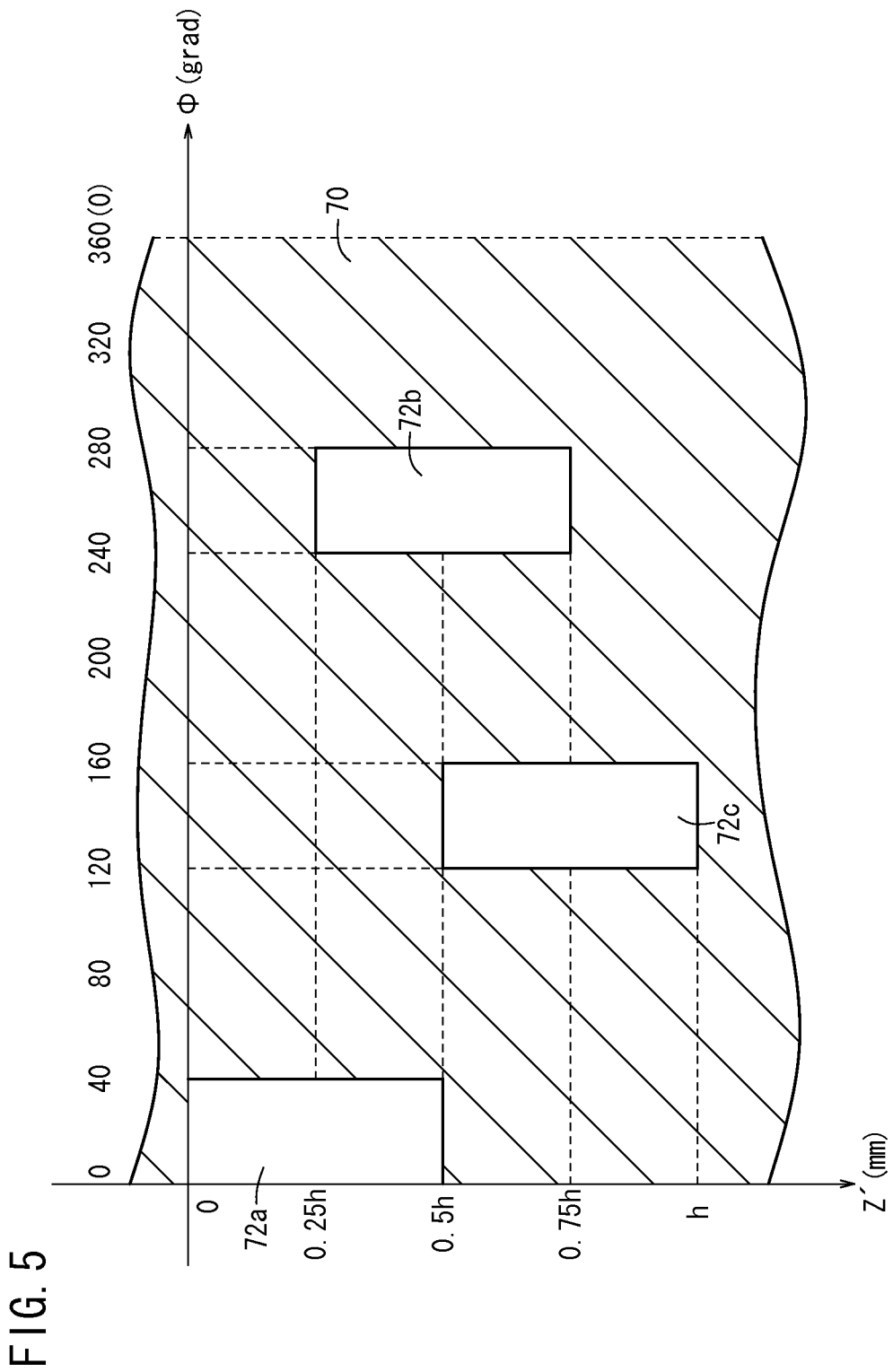
FIG. 5 is a fragmentary developed view of a side wall of an inner tube shown in FIG. 3.

FIG. 2 is an enlarged front elevational view of the probe 14 shown in FIG. 1. FIG. 3 is a cross-sectional view of the probe 14 taken along line III-III of FIG. 2. FIG. 4 is a cross-sectional view of the probe 14 taken along line IV-IV of FIG. 2. FIG. 5 is a fragmentary developed view of a side wall of an inner tube 52 shown in FIG. 3. For an easier understanding of the technical features of the present invention, the biopsy needle 10 is shown as exaggerated in size.

As shown in FIGS. 2 and 3, the probe 14 has a hollow casing 40 for housing part of a proximal end portion of the biopsy needle 10. The casing 40 is of a substantially hollow cylindrical shape and is made of a resin material. The casing 40 includes a substantially rectangular box 42 projecting laterally and extending in an axial direction of the probe 14. The box 42 supports on its flat top surface operating switches 44 including a slide switch 46 and a push switch 48.

As shown in FIG. 3, the biopsy needle 10 has an outer tube 50, an inner tube 52, and a tube cutter 54 which are successively arranged radially inwardly in the order named and disposed concentrically around a central axis 56 of the biopsy needle 10. Therefore, the biopsy needle 10 is of a triple-tube structure (see FIG. 4). The central axis 56 extends in the directions indicated by the arrow Z', i.e., the Z' directions. Of the Z' directions, the direction toward a distal end of the biopsy needle 10 is defined as the Z'1 direction, and the direction toward a proximal end of the biopsy needle 10 as the Z'2 direction.

The outer tube 50, which is made of a metal, is of a substantially hollow cylindrical shape and is open at its proximal end. The outer tube 50 has an externally threaded outer wall surface 58 on its proximal end portion for threaded engagement with the casing 40.

The outer tube 50 has a substantially conical cutting tip 60 on its distal end. The cutting tip 60 has a sharp edge for being inserted into the object 18. The outer tube 50 has an opening 64 defined in a side wall 62 thereof. The opening 64 will hereinafter be referred to as "an outer opening 64". The outer opening 64 is of a substantially rectangular shape which is elongate in the Z' directions.

The inner tube 52 is made of a metal and is of a substantially hollow cylindrical shape. The inner tube 52 is open at a proximal end 66 thereof and has a circular bottom 68 at a distal end thereof which is opposite to the proximal end 66. The inner tube 52 is angularly movable about the central axis 56 and/or axially movable in the Z' directions.

As shown in FIG. 5, the inner tube 52 has three openings 72a, 72b, 72c defined in a side wall 70 thereof. The openings 72a, 72b, 72c will hereinafter be referred to as "inner openings 72a, 72b, 72c". The inner openings 72a, 72b, 72c are of a substantially rectangular shape which is elongate in the Z' directions and are identical in shape to each other. In FIG. 5, the horizontal axis represents angles in a circumferential direction (hereinafter referred to as "φ direction") of the inner tube 52, and the vertical axis represents positions along the Z' directions.

The inner openings 72a, 72b, 72c are disposed in respective positions each angularly spaced from a next one by a predetermined angle Δφ=120 degrees along the φ direction. Each of the inner openings 72a, 72b, 72c has a width of Δφ=40 degrees along the φ direction. Therefore, the inner openings 72a, 72b, 72c do not overlap each other along the Z' direction. Each of the inner openings 72a, 72b, 72c is spaced from a next one by a predetermined distance ΔZ'=0.25 h along the Z'1 direction.

For illustrative purposes, each of the inner openings 72a, 72b, 72c is illustrated as a rectangular opening without rounded corners in FIG. 5 and also FIGS. 7A through 8C to be described later, rather than a rectangular opening having rounded corners shown in FIG. 2. This also holds true for the outer opening 64.

In FIGS. 2 through 4, the outer opening 64 defined in the outer tube 50 and the inner opening 72a defined in the inner tube 52 overlap each other, jointly providing a single communication port 74 which communicates with the interior of the inner tube 52.

As shown in FIG. 3, the tube cutter 54 is made of a metal and is of a substantially hollow cylindrical shape. The tube cutter 54 is open at both distal and proximal ends thereof. The tube cutter 54 has a sharply polished cutting face 78 on a side edge of a side wall 76 thereof at its distal end. The tube cutter 54 is angularly movable about the central axis 56 at high speed and axially movable in the Z' directions.

The casing 40, in which the biopsy needle 10 is mounted, has a circular opening 80 defined in an end thereof and a flange 82 disposed around the circular opening 80 and projecting in the φ direction. The flange 82 has an internally threaded wall surface 84 which is held in threaded engagement with the externally threaded outer wall surface 58 of the outer tube 50. The outer tube 50 is thus removably threaded in the casing 40.

The casing 40 has a first chamber 86 defined therein for housing therein the proximal end portion of the biopsy needle 10. The first chamber 86 includes a bottom wall 88 having an inner wall surface to which a hollow cylindrical sample holder 90 made of a resin material is fixed.

A joint 94 is interposed between an end 92 of the sample holder 90 in the Z'1 direction and the proximal end 66 of the inner tube 52. The joint 94, which is bellows-shaped, is extensible and contractible along the Z' directions. The joint 94 thus functions as a guide member for guiding a fluid (object) that is present in the inner tube 52 into the sample holder 90. The sample holder 90 has a horn-shaped protrusion 96 integral with an inner wall surface thereof near the end 92 thereof. The space formed within the sample holder 90 by the horn-shaped protrusion 96 is progressively greater in diameter toward the end 92.

The sample holder 90 also has a circular bottom wall 100 near the other end 98 thereof in the Z'2 direction. The bottom wall 100 is spaced a certain distance from the bottom wall 88 of the casing 40. The bottom walls 88, 100 and the other end 98 of the sample holder 90 jointly define a gap 102 therebetween. The bottom wall 100 has four circular holes 104 (see FIG. 4) defined therein which communicate with the gap 102. A connector 106 through which an end of the aspiration tube 22 is connected to the gap 102 is fitted over the outer wall surface of the bottom wall 88 of the casing 40.

An inner lid 108 is openably and closably mounted on a side wall of the sample holder 90. An outer lid 110 is openably and closably mounted on a side wall of the casing 40 in substantial positional alignment with the inner lid 108.

The casing 40 further includes a second chamber 112 that is defined in the box 42. The second chamber 112 houses therein an actuator 114, a drive circuit 116, and an I/F (interface) 118.

The actuator 114 is mechanically coupled to the inner tube 52 and the tube cutter 54. The actuator 114 rotates the inner tube 52 about the central axis 56 and moves the inner tube 52 back and forth in the Z' directions. The actuator 114 also rotates the tube cutter 54 about the central axis 56 at high speed and moves the tube cutter 54 back and forth in the Z' directions. The actuator 114 may be any of various drive mechanisms available in the art.

The drive circuit 116 controls driving of the actuator 114 in response to an operation of the operating switches 44. The drive circuit 116 may control driving of the actuator 114 in response to a control signal received from the main unit body 16 via the cable 20 and the I/F 118.

The sample extracting unit 12 is constructed as described above. Operation of the sample extracting unit 12 will be described below with reference to FIGS. 6A through 9C as well as FIGS. 1 through 5.

A user or robot arm which grips the probe 14 moves the probe 14 to insert the biopsy needle 10 into the object 18 to be inspected. Then, the user operates the slide switch 46 (see FIGS. 2 and 3), and accordingly the drive circuit 116 moves the actuator 114 by a given distance. The motion of the actuator 114 is converted into a rotary and axial motion of the inner tube 52, which is mechanically connected to the actuator 114.

As the inner tube 52 rotates or axially moves, the position of the communication port 74 changes depending on the relative positional relationship between the outer tube (the outer opening 64) and the inner tube 52 (the inner openings 72a through 72c). The position of the communication port 74 as it changes upon rotation of the inner tube 52 in the φ direction will be described in detail below with reference to FIGS. 6A through 8C.

Figure 6A:
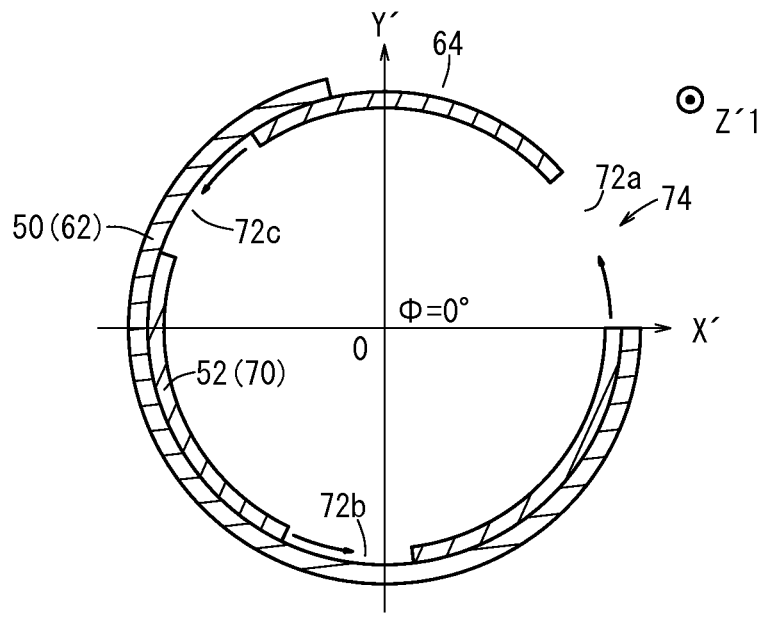
FIGS. 6A and 6B are cross-sectional views of the probe taken along line VI-VI of FIG. 2.
Figure 6B:
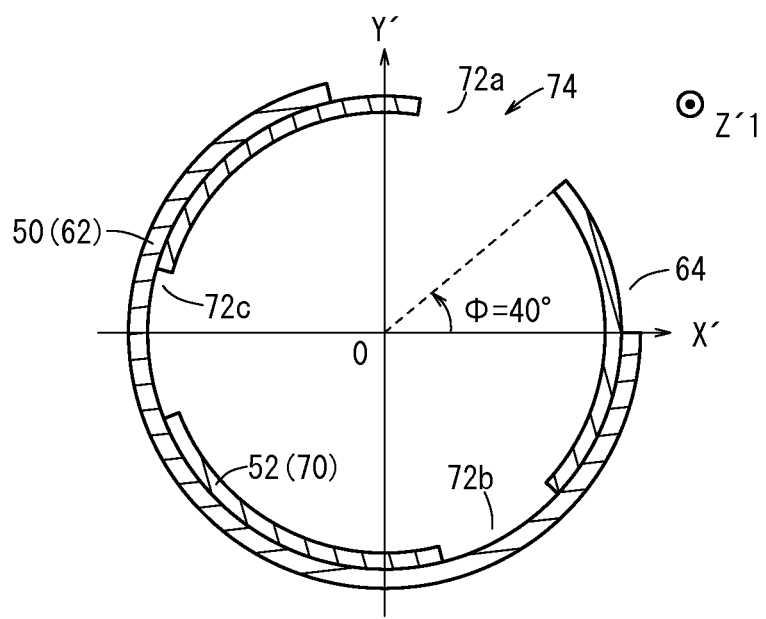

FIGS. 6A and 6B are cross-sectional views, partly omitted from illustration, of the probe 14 taken alone line VI-VI of FIG. 2. In an X'Y'Z' coordinate system, the position of the central axis 56 that lies in a plane including a shorter side of the outer opening 64 on its distal end side in the Z'1 direction is used as a reference (origin O). In the φ direction, the state wherein the upper left corner of the outer opening 64 and the upper left corner of the inner opening 72a are aligned with each other is used as a reference (φ=0 degree) (see FIG. 7A). FIGS. 6A and 6B show the relative positional relationship between the outer tube 50 and the inner tube 52 respectively at φ=0 degree and φ=40 degrees.

FIGS. 7A through 8C are fragmentary views showing the relative positional relationship between the side wall 70 of the inner tube 52 which has been turned through given angles and the side wall 62 of the outer tube 50. In FIGS. 7A through 8C, the cross-hatched area represents an area where both the side wall 62 of the outer tube 50 and the side wall 70 of the inner tube 52 are present. The first hatched area (an area hatched by oblique lines extending downwardly to the right) represents an area where only the side wall 62 of the outer tube 50 is present. The second hatched area (an area hatched by oblique lines extending downwardly to the left) represents an area where only the side wall 70 of the inner tube 52 is present. The blank area represents an area where neither the side wall 62 of the outer tube 50 nor the side wall 70 of the inner tube 52 is present, i.e., it represents the communication port 74 which communicates with the interior of the inner tube 52.

As shown in FIG. 7A, in a state where the outer opening 64 and the inner opening 72a overlap each other (the inner tube 52 is turned through 0 degree, hereinafter referred to as "state 1"), a single rectangular communication port 74 is defined in a range represented by ($0 \leq \phi \leq 40$) and ($0 \leq Z' \leq 0.5$ h). Since the other inner openings 72b, 72c fully overlap the side wall 62 of the outer tube 50, no communication port 74 is defined in the positions of the inner openings 72b, 72c.

In the case where only the inner tube 52 is turned through 40 degrees in the φ direction from the state 1, the state 1 changes to a state 2 (the inner tube 52 has been turned through 40 degrees). In the state 2, as in the state 1, the outer opening 64 and the inner opening 72a overlap each other, and a single rectangular communication port 74 is defined in a range represented by (40≤φ≤80) and (0≤Z'≤0.5 h), as shown in FIG. 7B.

In the case where only the inner tube 52 is further turned through 30 degrees in the φ direction from the state 2, the state 2 changes to a state 3 (the inner tube 52 has been turned through 70 degrees). In the state 3, as in the states 1 and 2, the outer opening 64 and the inner opening 72a overlap each other, and a single rectangular communication port 74 is defined in a range represented by (70≤φ≤110) and (0≤Z'≤0.5 h), as shown in FIG. 7C.

In the case where only the inner tube 52 is further turned through 50 degrees in the φ direction from the state 3, the state 3 changes to a state 4 (the inner tube 52 has been turned through 120 degrees).

Figure 8A:
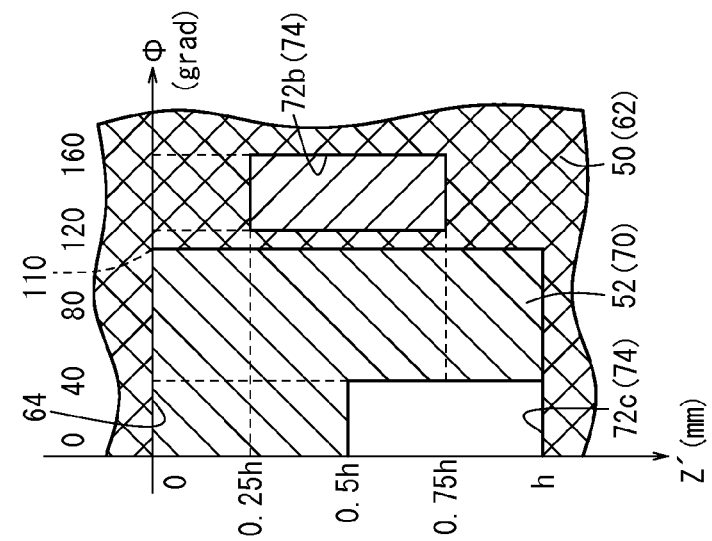
FIGS. 8A through 8C are fragmentary developed side elevational views showing relative positional relationships between the side wall of the inner tube which has been turned through given angles and the side wall of the outer tube.

In the state 4, as shown in FIG. 8A, unlike the states 1 through 3, the outer opening 64 and the inner opening 72b overlap each other, and a single rectangular communication port 74 is defined in a range represented by (0≤φ≤40) and (0.25 h≤Z'≤0.75 h). Since the other inner openings 72a, 72c fully overlap the side wall 62 of the outer tube 50, no communication port 74 is defined in the positions of the inner openings 72a, 72c.

Figure 8B:
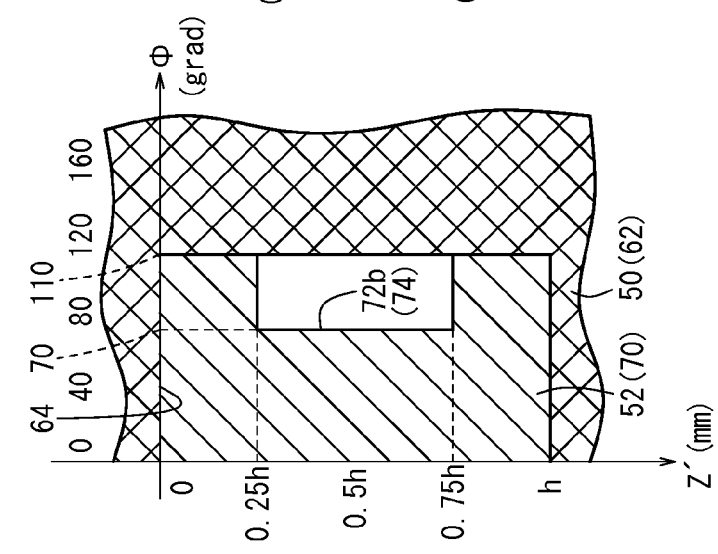

In the case where only the inner tube 52 is turned through 70 degrees in the φ direction from the state 4, the state 4 changes to a state 5 (the inner tube 52 has been turned through 190 degrees). In the state 5, as in the state 4, the outer opening 64 and the inner opening 72b overlap each other, and a single rectangular communication port 74 is defined in a range represented by (70≤φ≤110) and (0.25 h≤Z'≤0.75 h), as shown in FIG. 8B.

Figure 8C:
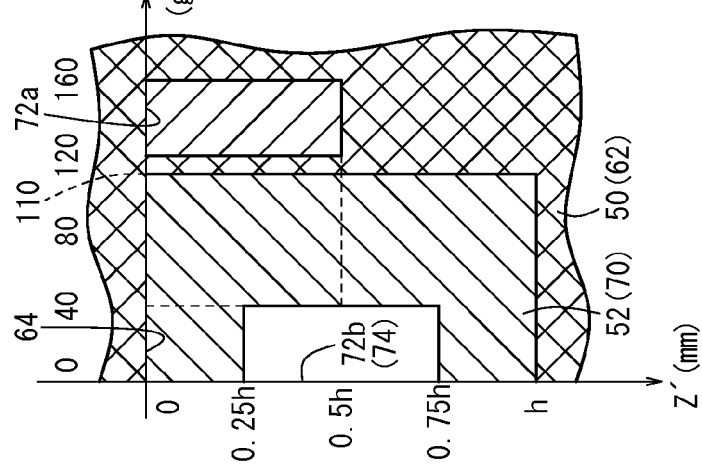

In the case where only the inner tube 52 is further turned through 50 degrees in the φ direction from the state 5, the state 5 changes to a state 6 (the inner tube 52 has been turned through 240 degrees). In the state 6, unlike the states 1 through 5, the outer opening 64 and the inner opening 72c overlap each other, and a single rectangular communication port 74 is defined in a range represented by (0≤φ≤40) and (0.5 h≤Z'≤h), as shown in FIG. 8C. Since the other inner openings 72a, 72b fully overlap the side wall 62 of the outer tube 50, no communication port 74 is defined in the positions of the inner openings 72a, 72b.

As shown in FIGS. 7A through 7C, the communication port 74 whose area is constant at all times can be continuously shifted in the φ direction, i.e., in the circumferential direction, while being held in a constant position in the Z' directions, i.e., in the axial directions (0≤Z'≤0.5 h). In addition, as shown in FIGS. 7A, 8A, and 8C, the communication port 74 whose area is constant at all times can be shifted to given positions in the Z' directions while being held in a constant position in the φ direction (0≤φ≤40). In other words, as shown in FIGS. 7A through 8C, the communication port 74 whose area is constant at all times can be brought to substantially all positions in a range where the outer opening 64 is present.

The outer opening 64 and a portion of the inner opening 72a or the inner opening 72b or 72c may be caused to overlap each other by turning the inner tube 52 through an intermediate angle. For example, in the case where the inner tube 52 is turned through −20 degrees or 340 degrees, the area of the communication port 74 is set to about one-half of the area shown in FIG. 7A. Therefore, the communication port 74 can be set to desired areas with greater freedom.

In this manner, the user positions the communication port 74 based on a predetermined decision criterion.

As shown in FIG. 3, in response to the pressing operation of the switch 32 (see FIG. 1), the aspirator 24 of the main unit body 16 starts an aspiration process. At this time, a mass, which is denoted by 140 in FIG. 9C, including a fluid such as air, etc. in the vicinity of the communication port 74 is aspirated through the inner tube 52, the tube cutter 54, the joint 94, the sample holder 90, the circular holes 104, the gap 102, the aspiration tube 22 and the opening 26 toward the aspirator 24.

Figure 9A:
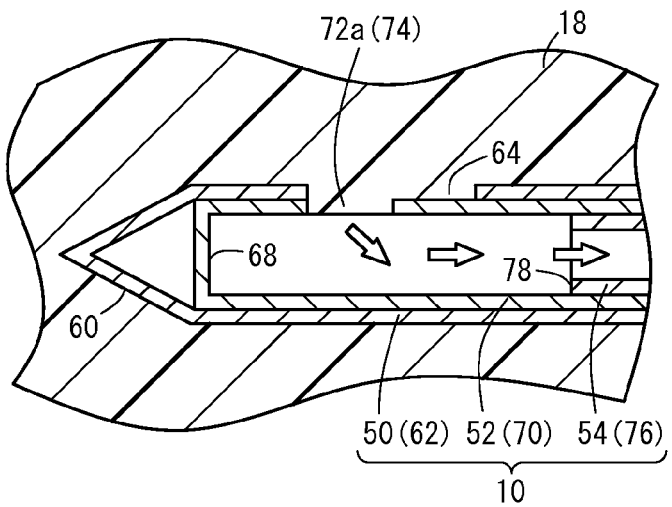
FIGS. 9A through 9C are fragmentary cross-sectional views showing a succession of state changes of the probe until a portion of an object to be examined is aspirated into the inner tube and cut off.
Figure 9B:
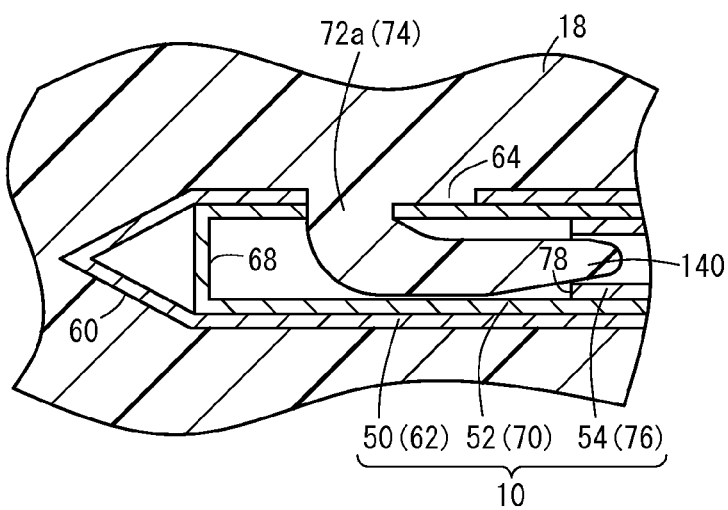
Figure 9C:
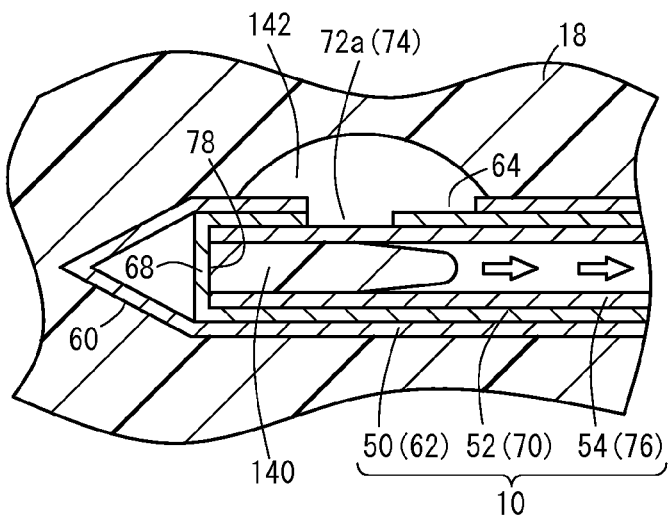

Specifically, as shown in FIGS. 9A and 9B, under a condition where the biopsy needle 10 is inserted in the object 18, the mass 140 near the communication port 74 of the needle 10 is subjected to an aspirating pressure exerted from the aspirator 24 through the communication port 74, and then the mass 140 (see FIG. 9C) in the vicinity of the communication port 74 is gradually drawn into the inner tube 52 and then reaches its steady state.

The user operates the push switch 48 (see FIGS. 2 and 3), and accordingly the drive circuit 116 moves the actuator 114 by a given distance. The motion of the actuator 114 is converted into a rotary and axial motion of the tube cutter 54 that is connected to the actuator 114. Specifically, the user presses the push switch 48, whereby the tube cutter 54 in the inner tube 52 is axially moved along the Z'1 direction while rotating in the φ direction at high speed. As a result, the cutting face 78 of the tube cutter 54 is pressed against the inner wall surface of the bottom 68, and then the mass 140 which is introduced into the inner tube 52 is cut off from the object 18 (see FIG. 9C).

Since the communication port 74 is temporarily closed by the side wall 76 of the tube cutter 54, the remaining region of the object 18 returns to its original position under its restoring force, leaving a cavity 142 in a region which was occupied by the mass 140.

The mass 140 which is separated from the object 18 is delivered toward the proximal end portion of the biopsy needle 10 under the aspirating pressure generated by the aspirator 24. The mass 140 is then introduced through the joint 94 into the sample holder 90, and blocked by the bottom wall 100 and held in the sample holder 90.

Since the bottom wall 100 has the plural circular holes 104, the aspirating action through the communication port 74 continues through some of the circular holes 104 that are not closed by the mass 140. The horn-shaped protrusion 96 which is positioned near the end 92 of the sample holder 90 prevents the mass 140 held in the sample holder 90 from flowing back toward the biopsy needle 10.

The user operates the operating switches 44 (see FIGS. 2 and 3), and accordingly the tube cutter 54 is retracted in the Z'2 direction or the inner tube 52 is moved to its original position. Then, the user operates the switch 32 (see FIG. 1) to stop the aspiration process by the aspirator 24.

Thereafter, the user opens the outer lid 110 (see FIG. 3) of the outer tube 50 and then opens the inner lid 108 of the inner tube 52, exposing the mass 140 held in the sample holder 90 to the outside. The user can now extract the mass 140 as a sample from the probe 14.

As described above, the biopsy needle 10 according to the present invention includes a plurality of inner openings 72a through 72c defined in the side wall 70 of the inner tube 52 and at least one outer opening 64 defined in the side wall 62 of the outer tube 50. As the inner tube 52 moves with respect to the outer tube 52, the outer opening 64 overlaps either one of the inner openings 72a through 72c, providing a single communication port 74 which communicates with the interior of the inner tube 52. The range, i.e., the position and size, of the communication port 74 can be set more flexibly. Therefore, access of the biopsy needle 10 to a biopsy region of the object 18 can be optimized. Thus, the biopsy needle 10 can extract a tissue sample without the need for subsequent re-insertion into the object 18 even if the biopsy needle 10 has been inserted into the object 18 at a position spaced from the biopsy region.

As the single outer opening 64 is defined in the side wall 62 of the outer tube 50, the side wall 70 of the inner tube 52 is exposed to the exterior of the outer tube 50 through only one place, i.e., the single outer opening 64. Consequently, the entry of a liquid substance between the outer tube 50 and the inner tube 52 is greatly limited.

Basic structural details of a mammographic apparatus (biopsy apparatus) 200 according to a preferred embodiment which incorporates the sample extracting unit 12 will be described below with reference to FIGS. 10 through 13.

The mammographic apparatus 200 basically includes an upstanding base 202, a vertical arm 206 fixed to the distal end of a swing shaft 204 disposed substantially centrally on the base 202, a radiation source housing unit 216 housing therein a radiation source 214 for applying radiations 212a, 212b (see FIG. 12, collectively referred to as "radiation 212" in FIG. 11) to a breast 210 as an object to be examined of an examinee (subject) 208 and fixed to an upper end of the arm 206, an examination base 220 mounted on the lower end of the arm 206 and housing therein a solid-state detector (radiation detector) 218 for detecting the radiation 212 which has passed through the breast 210, a compression plate 222 for compressing and holding the breast 210 against the examination base 220, and a biopsy hand assembly 226 for extracting a tissue sample from a biopsy region or mass 224 of the breast 210, the biopsy hand assembly 226 being mounted on the compression plate 222.

Figure 10:
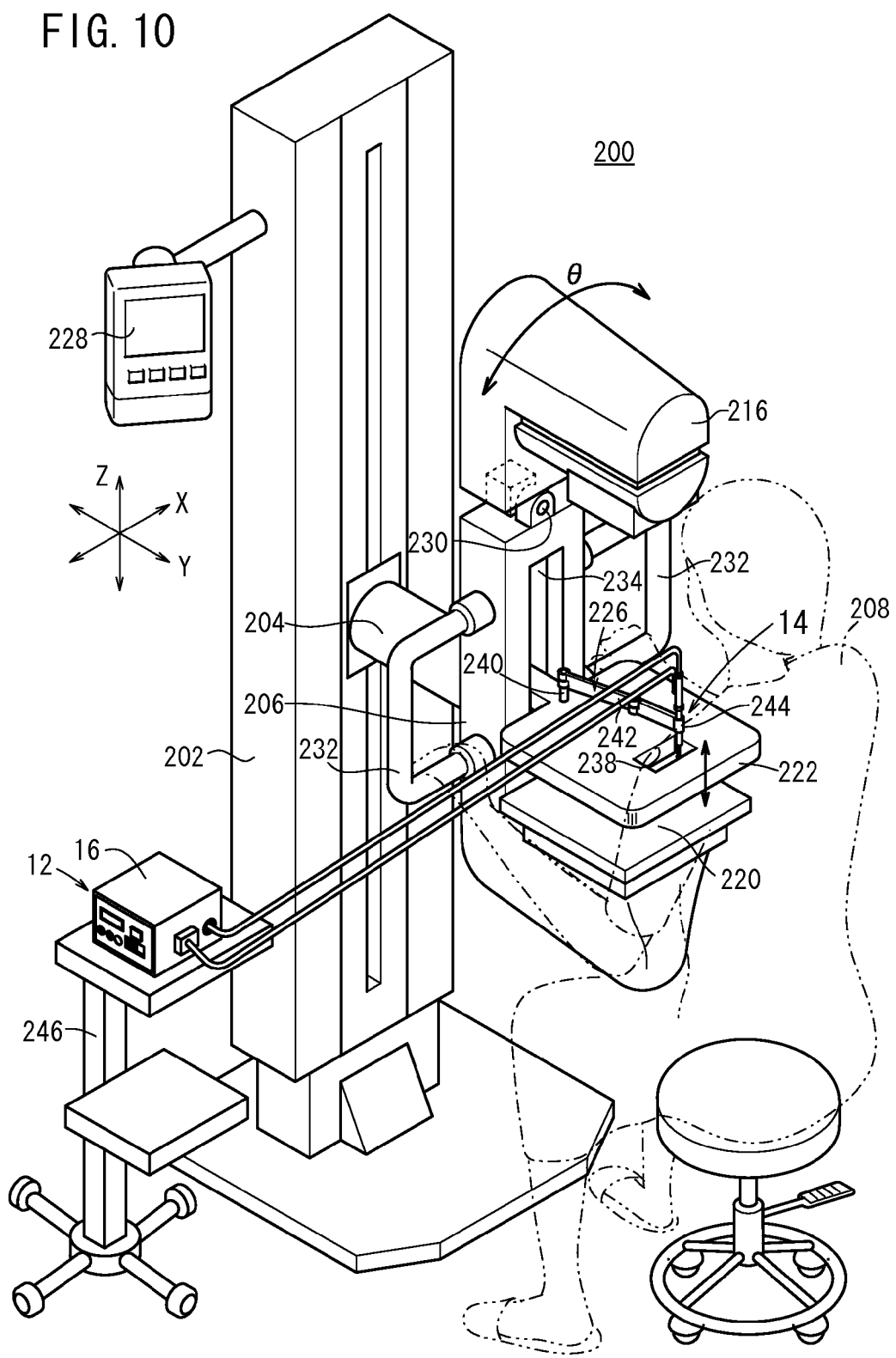
FIG. 10 is a perspective view of a mammographic apparatus which incorporates the sample extracting unit shown in FIG. 1.
Figure 11:
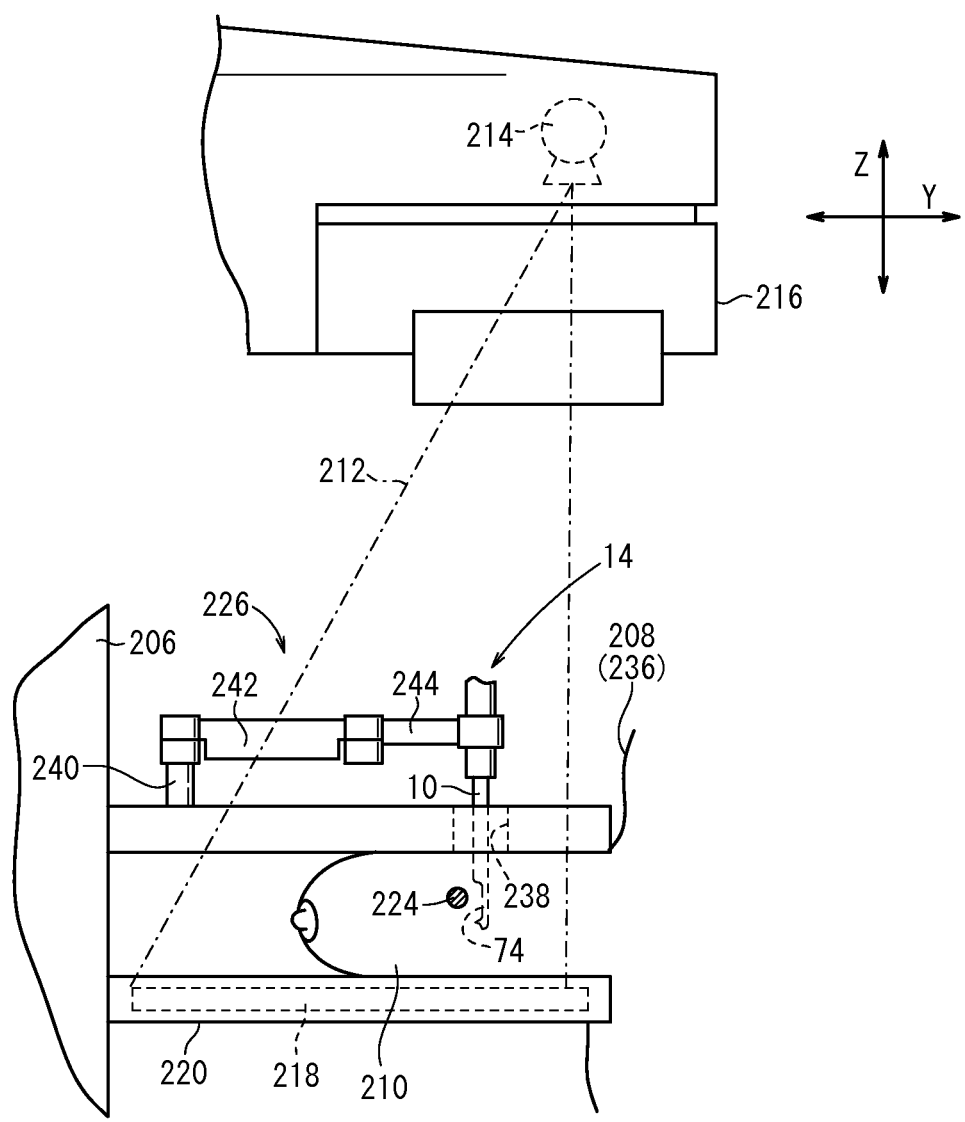
FIG. 11 is a fragmentary side elevational view of the mammographic apparatus shown in FIG. 10.

In FIGS. 10 and 11, the mammographic apparatus 200 applies the radiation 212 to the breast 210 of the examinee 208 and extracts a tissue sample from the biopsy region 224 while the breast 210 of the examinee 208 who is in a sitting position is compressed and secured by the compression plate 222 and the examination base 220. To the base 202, there is connected a display control panel 228 for displaying image capturing conditions representing an image capturing region, etc. of the examinee 208, ID information of the examinee 208, etc., and also for setting the image capturing conditions, the ID information, etc. if necessary.

The arm 206, to which the radiation source housing unit 216 and the examination base 220 are secured, is angularly moved about the swing shaft 204, whereby the direction of the radiation source housing unit 216 and the examination base 220 with respect to the breast 210 of the examinee 208 is adjusted. The radiation source housing unit 216 is operatively coupled to the arm 206 by a hinge 230 and can be turned about the hinge 230 in the directions indicated by the arrow θ independently of the examination base 220.

Handles 232, which are gripped by the examinee 208, are mounted on respective sides of the arm 206 and face away from each other along directions indicated by the arrow X. The compression plate 222 has a proximal end inserted in a groove 234 defined in the arm 206. The compression plate 222 is disposed between the radiation source housing unit 216 and the examination base 220. The compression plate 222 is vertically displaceable in the directions indicated by the arrow Z.

The biopsy hand assembly 226 is mounted on an upper surface of the compression plate 222, which faces toward the radiation source 214, in the vicinity of the groove 234. The compression plate 222 has a rectangular opening 238 defined therein near a chest wall 236 (see FIG. 11) of the examinee 208, for allowing the biopsy hand assembly 226 to extract a tissue sample from the biopsy region 224 of the breast 210. The compression plate 222 may be detachable from the groove 234.

The biopsy hand assembly 226 comprises a post 240 fixedly mounted on the compression plate 222, a first arm 242 having an end pivotally supported on the post 240 and angularly movable about the post 240 along the upper surface of the compression plate 222, and a second arm 244 having an end pivotally supported on the other end of the first arm 242 and angularly movable about the other end of the first arm 242 along the upper surface of the compression plate 222. The biopsy needle 10, i.e., part of the probe 14, which is movable in the directions indicated by the arrow Z is mounted on the other end of the second arm 244. The main unit body 16 (see FIG. 1) to which the biopsy needle 10 is connected is placed on a rack 246.

The biopsy needle 10 includes the communication port 74 for aspirating and extracting a sample tissue, e.g., a calcified tissue, from the biopsy region 224 of the breast 210. The communication port 74 can be positioned in the vicinity of the biopsy region 224 by moving the first arm 242 and the second arm 244 of the biopsy hand assembly 226 in an X-Y plane along the upper surface of the compression plate 222 and also by moving the biopsy needle 10 in the directions indicated by the arrow Z.

Figure 12:
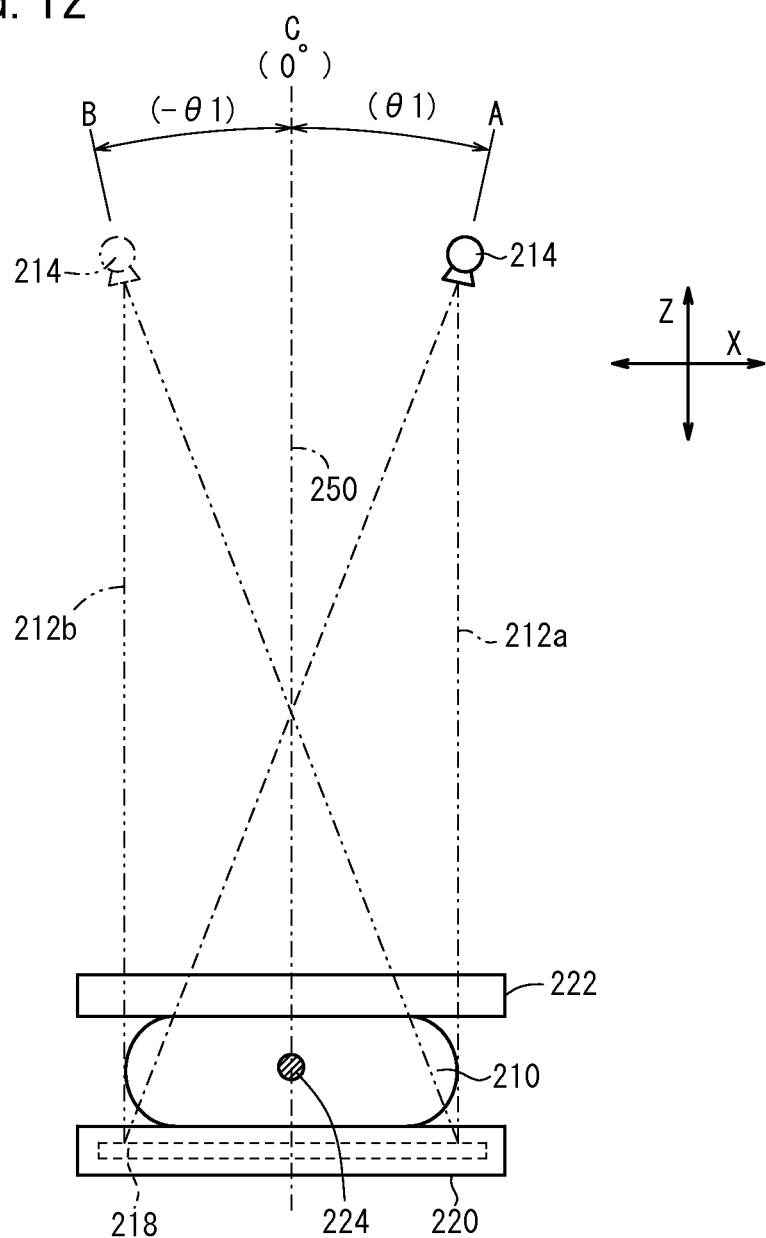
FIG. 12 is a schematic front elevational view illustrative of a stereoscopic image capturing process which is performed by the mammographic apparatus shown in FIG. 10.

As shown in FIG. 12, the mammographic apparatus 200 performs a stereoscopic image capturing process by applying radiations 212a, 212b to the breast 210 from the radiation source 214 which is disposed in positions A and B obliquely to a vertical axis (central axis) 250 of the solid-state detector 218. The solid-state detector 218 detects the radiations 212a, 212b that have passed through the breast 210 and converts the detected radiations 212a, 212b into respective radiographic images (stereoscopic image).

In the mammographic apparatus 200, the number of stereoscopic images that are captured and the order in which such images are captured are set as desired by the user. The radiation source 214 is moved angularly between the positions A and B by turning the radiation source housing unit 216 about the hinge 230 (see FIG. 10), as described above. According to the present embodiment, the radiation source 214 applies the radiations 212a, 212b from the respective positions A and B in a condition where the radiation source 214 is in the positions A and B. However, the mammographic apparatus 20 may perform another stereoscopic image capturing process, in which the radiation source 214 applies radiations 212a, 212b from the position A and another position C on the vertical axis 250 in a condition where the radiation source 214 is in the positions A and C. Still another stereoscopic image capturing process may be performed, in which the radiation source 214 applies radiations 212a, 212b from the respective positions B and C in a condition where the radiation source 214 is in the positions B and C.

Figure 13:
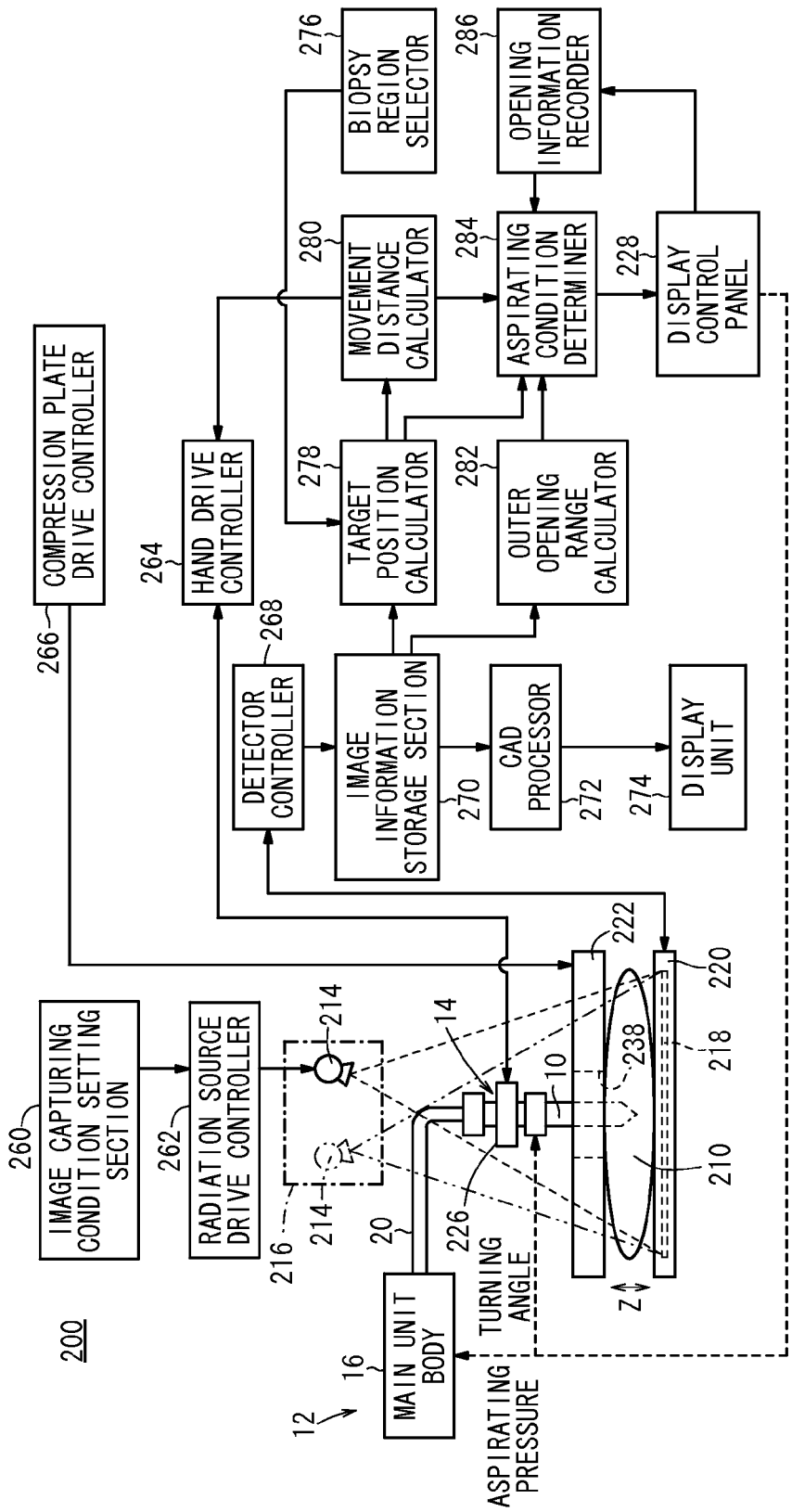
FIG. 13 is a block diagram of a control circuit of the mammographic apparatus shown in FIG. 10.

FIG. 13 is a block diagram of a control circuit of the mammographic apparatus 200.

As shown in FIG. 13, the mammographic apparatus 200 includes an image capturing condition setting section 260, a radiation source drive controller 262, a hand drive controller 264, a compression plate drive controller 266, a detector controller 268, an image information storage section 270, a CAD (Computer Aided Diagnosis) processor 272, a display unit 274, a biopsy region selector 276, a target position calculator (position calculator) 278, a movement distance calculator 280, an outer opening range calculator 282, an aspirating condition determiner 284, and an opening information recorder 286.

The image capturing condition setting section 260 sets image capturing conditions including a tube current and a tube voltage of the radiation source 214, the types of a target and a filter included in the radiation source 214, irradiation dosage and irradiation time of the radiations 212a, 212b, angles (imaging angles at the positions A, B, C) of the radiation source 214 with respect to the vertical axis of the solid-state detector 218 along the directions indicated by the arrow Z in stereoscopic image capturing processes. The radiation source drive controller 262 controls operation of the radiation source 214 according to the image capturing conditions described above. The hand drive controller 264 controls the biopsy hand assembly 226 (see FIGS. 10 and 11) to move the biopsy needle 10, i.e., the probe 14, to a desired position. The compression plate drive controller 266 controls the compression plate 222 to move in the directions indicated by the arrow Z. The detector controller 268 controls the solid-state detector 218 to store radiation images converted by the solid-state detector 218 in the image information storage section 270.

As shown in FIG. 12, the mammographic apparatus 200 performs a stereoscopic radiographic image capturing process on the breast 210 at the positions A and B. More specifically, the radiation source housing unit 216 is angularly moved about the hinge 230 (see FIG. 10) so as to place the radiation source 214 selectively in the positions A and B for the image capturing process. The image information storage section 270 stores two radiographic images of the breast 210 which are captured respectively at the positions A and B.

The CAD processor 272 processes the two radiographic images stored in the image information storage section 270, and displays the processed radiographic images on the display unit 274. At this time, the CAD processor 272 may display the processed radiographic images on the display control panel 228.

The biopsy region selector 276 is in the form of a pointing device such as a mouse or the like. In the case where the doctor or radiological technician sees the two radiographic images displayed on the display unit 274, the doctor or radiological technician can select a biopsy region 224 from which a sample tissue is to be removed among a plurality of biopsy regions 224 in the displayed two radiographic images, using the pointing device (biopsy region selector 276). At this time, using the biopsy region selector 276, the doctor or radiological technician selects a biopsy region 224 among a plurality of biopsy regions 224 in one of the displayed two radiographic images, and also selects a corresponding biopsy region 224 among a plurality of biopsy regions 224 in the other displayed radiographic image.

The target position calculator 278 calculates a three-dimensional position of the biopsy region 224 based on the positions of the biopsy regions 224 selected by the biopsy region selector 276. The target position calculator 278 also calculates positional information of the biopsy needle 10 which has been moved by the hand drive controller 264, i.e., the three-dimensional position of the distal end of the cutting tip 60 (see FIGS. 3 and 4). The three-dimensional positions of the biopsy region 224 and the biopsy needle 10 can be calculated according to a known process in the stereoscopic radiographic image capturing process.

The movement distance calculator 280 calculates a movement distance that the biopsy needle 10 is to move with respect to the biopsy region 224, based on the three-dimensional positions of the biopsy region 224 and the biopsy needle 10, e.g., the distal end of the cutting tip 60, which are calculated by the target position calculator 278. The hand drive controller 264 moves the biopsy needle 10 based on the distance calculated by the movement distance calculator 280, so that the biopsy needle 10 can extract a sample tissue from the biopsy region 224.

The outer opening range calculator 282 calculates a presence range in which the outer opening 64 of the outer tube 50 is present, using the two radiographic images stored in the image information storage section 270. A three-dimensional position of the outer opening 64 may be calculated according to a known process in the stereoscopic radiographic image capturing process, or may be calculated based on the relative positional relationship between the biopsy needle 10 and other regions.

The aspirating condition determiner 284 determines an aspirating condition (recommended value) for aspirating the biopsy region 224 based on the three-dimensional position of the biopsy region 224 that is calculated by the target position calculator 278 and the presence range of the outer opening 64 that is calculated by the outer opening range calculator 282.

According to a first example, the aspirating condition determiner 284 may determine a position and attitude of the communication port 74 which provides the shortest distance to the biopsy region 224, based on the relative positional relationship between a given position of the outer opening 64, e.g., the position of the center of gravity thereof, and the biopsy region 224. The position and attitude of the communication port 74 thus determined can increase the possibility to aspirate the biopsy region 224 in one cycle.

According to a second example, the aspirating condition determiner 284 may determine an aspirating pressure (lower limit value) which makes it possible to aspirate the biopsy region 224, based on a given relational expression between the distance between the outer opening 64 and the biopsy region 224 and the aspirating pressure. The aspirating pressure thus determined can minimize the amount of tissue samples extracted from living body regions other than the biopsy region 224.

According to a third example, the aspirating condition determiner 284 may determine a specific control value in view of inherent characteristics of the sample extracting unit 12 (the biopsy needle 10 and the aspirator 24). The specific control value may be, for example, the movement distance of the inner tube 52, i.e., the displacement distance that the inner tube 52 is to be displaced in the Z' directions and the turning angle through which it is to be angularly moved, or a setting value for the aspirating pressure to be developed by the aspirator 24.

In order to determine the aspirating condition more strictly, the aspirating condition determiner 284 may refer to opening information about the biopsy needle 10. The opening information recorder 286 may record in advance opening information related to the types and serial numbers of various biopsy needles 10, and supply the opening information depending on the type of the biopsy needle 10 which is indicated by the display control panel 228 to the aspirating condition determiner 284. The aspirating condition determiner 284 can directly convert the relative positional relationship between the outer opening 64 and the biopsy region 224 into a movement distance of the inner tube 52 by referring to the supplied opening information.

Figure 14:
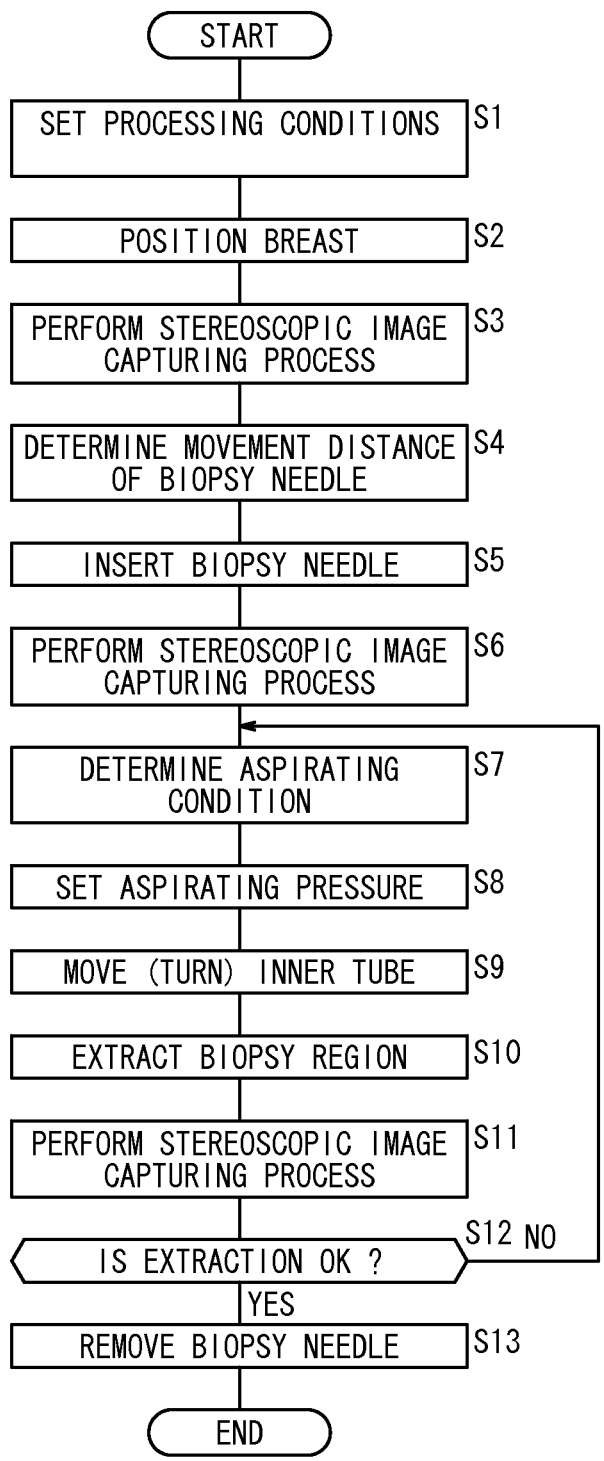
FIG. 14 is a flowchart of an operation sequence of the mammographic apparatus shown in FIG. 10.

The mammographic apparatus 200 according to the present embodiment is basically constructed as described above. Now, an operation sequence of the mammographic apparatus 200 to perform a biopsy procedure will be described below with reference to a flowchart shown in FIG. 14.

In step S1, using the image capturing condition setting section 260 (see FIG. 13), a doctor as a user sets processing conditions including subject information about the age, sex, body type, subject identification number, etc. of the examinee 208, image capturing conditions for capturing radiographic image information, an image capturing method, a movement limiting quantity for limiting movement of the biopsy hand assembly 226, and the type of the biopsy needle 10. These processing conditions may be displayed on the display control panel 228 for the doctor to confirm.

In step S2, the doctor positions the breast 210 of the examinee 208 according to the image capturing method. For example, the breast 210 may be imaged as a cranio-caudal view (CC) taken from above with the examination base 220 extending horizontally, a medio-lateral view (ML) taken outwardly from the center of the chest wall 236 with the examination base 220 extending vertically, or a medio-lateral oblique view (MLO) taken from an oblique view with the examination base 220 extending obliquely. After the breast 210 is placed in a given position, which faces the opening 238, on the examination base 220, the compression plate drive controller 266 moves the compression plate 222 toward the examination base 220 in the direction indicated by the arrow Z. As a result, the breast 210 is compressed and secured by the examination base 220 and the compression plate 222.

In step S3, the radiation source drive controller 262 energizes the radiation source 214 to perform a stereoscopic image capturing process on the breast 210. More specifically, the radiation source housing unit 216 is turned about the hinge 230, and the radiation source 214 is energized to apply the radiations 212a, 212b from the respective positions A and B (see FIG. 12) to the breast 210. The radiations 212a, 212b that have passed through the breast 210 are detected as two radiographic images by the solid-state detector 218 in the examination base 220. The detector controller 268 controls the solid-state detector 218 to acquire the two radiographic images therefrom, and temporarily stores the two radiographic images in the image information storage section 270. The CAD processor 272 processes the two radiographic images of the breast 210 stored in the image information storage section 270 into a stereoscopic image, and displays the stereoscopic image on the display unit 274 and/or the display control panel 228.

In step S4, the hand drive controller 264 actuates the biopsy hand assembly 226 to move the biopsy needle 10 to a suitable position. Specifically, while seeing the displayed stereoscopic image, the doctor operates the biopsy region selector 276 (pointing device such as a mouse, etc.) to indicate a lesion (target, biopsy region 224) from which a tissue sample is to be extracted, among a plurality of lesions in the displayed stereoscopic image. The target position calculator 278 calculates a three-dimensional position of the biopsy region 224 indicated in the displayed stereoscopic image, and outputs information of the calculated three-dimensional position to the movement distance calculator 280. The target position calculator 278 also calculates a three-dimensional position of the biopsy needle 10 in the displayed stereoscopic image, and outputs information of the calculated three-dimensional position to the movement distance calculator 280.

In step S5, the hand drive controller 264 controls the biopsy hand assembly 226 based on the movement distance of the biopsy needle 10, thereby inserting the biopsy needle 10 into the breast 210. More specifically, the hand drive controller 264 moves the first arm 242 and the second arm 244 in the X-Y plane thereby to position the biopsy needle 10 at a position facing the target or the biopsy region 224, i.e., at a position which faces toward the biopsy region 224 along the Z directions. Thereafter, the hand drive controller 264 moves the biopsy needle 10 toward the examination base 220. The biopsy needle 10 is inserted into the breast 210 so that the communication port 74 is positioned near the biopsy region 224, whereby the biopsy region 224 is included within the aspirating range or sample extracting range of the communication port 74.

In step S6, the radiation source drive controller 262 energizes the radiation source 214 to perform a stereoscopic image capturing process on the breast 210. The stereoscopic image capturing process which captures two radiographic images in step S6 is the same as the stereoscopic image capturing process performed in step S3, and will not be described in detail below. The two radiographic images captured in step S6 are temporarily stored in the image information storage section 270.

In step S7, the aspirating condition determiner 284 determines an aspirating condition for aspirating the biopsy region 224 based on the three-dimensional position of the biopsy region 224 that is calculated by the target position calculator 278 and the presence range of the outer opening 64 that is calculated by the outer opening range calculator 282. The aspirating condition may be determined according to any one of the first through third examples described above, or using the opening information recorded in the opening information recorder 286. The display control panel 228 displays the aspirating condition determined by the aspirating condition determiner 284 as a recommended value.

In step S8, the doctor sets an aspirating pressure for the aspirator 24 (see FIG. 1) housed in the main unit body 16. In a case where the doctor sets an aspirating pressure manually, the doctor operates the mode switcher 36 (see FIG. 1) to switch to "MANUAL" (manual mode) in advance, and then operates the condition setting part 34 to set a desired aspirating pressure value (see the broken-line arrow in FIG. 13) while seeing the recommended value displayed on the display control panel 228. In this manner, an accurate aspiration control process can be performed based on a combination of the range (position and size) of the communication port 74 and the aspirating pressure.

In step S9, the doctor sets a turning angle through which the inner tube 52 (see FIGS. 3 and 4) of the biopsy needle 10 is turned. In a case where the doctor sets a turning angle manually, then the doctor operates the slide switch 46 (see FIG. 2) of the probe 14 to move the communication port 74 to a desired position (see the broken-line arrow in FIG. 13) while seeing the recommended value displayed on the display control panel 228.

In step S10, the doctor extracts the biopsy region 224 from the breast 210 of the examinee 208 as a sample tissue. The sample extracting unit 12 operates as described above to draw the sample tissue from the biopsy region 224 near the communication port 74 into the inner tube 52 through the communication port 74. The biopsy region 224 is cut off as the mass 140 (see FIG. 9C) by the tube cutter 54 and held in the sample holder 90. The doctor opens the inner lid 108 and the outer lid 110, exposing the biopsy region 224 to the outside, and collects the sample tissue of the biopsy region 224 from the biopsy needle 10.

In step S11, the radiation source drive controller 262 energizes the radiation source 214 to perform a stereoscopic image capturing process on the breast 210. The stereoscopic image capturing process which captures two radiographic images in step S11 is the same as the stereoscopic image capturing process performed in step S3, and will not be described in detail below. The two radiographic images captured in step S11 are temporarily stored in the image information storage section 270.

In step S12, the doctor determines whether the biopsy region 224 has been extracted in its entirety or not, based on the two radiographic images captured by the stereoscopic image capturing process. Alternatively, the doctor may determine whether the biopsy region 224 has been extracted in its entirety or not by observing the sample tissue collected in step S10.

If the doctor judges that the biopsy region 224 has not been extracted in its entirety, then control returns to step S7 to repeat the aspirating process in steps S7 through S11. At this time, the biopsy needle 10 is not removed from the breast 210. The three-dimensional positions of the biopsy needle 10 and the biopsy region 224 are confirmed on the stereoscopic image, and the aspirating pressure of the aspirator 24 or the position of the communication port 74 is accordingly adjusted. Then, the biopsy region 224 is extracted again. In this manner, the extracting process is repeated.

The effectiveness of the process of extracting the biopsy region 224 by the method of controlling the biopsy needle 10 according to the present embodiment will be described below.

Figure 15B:
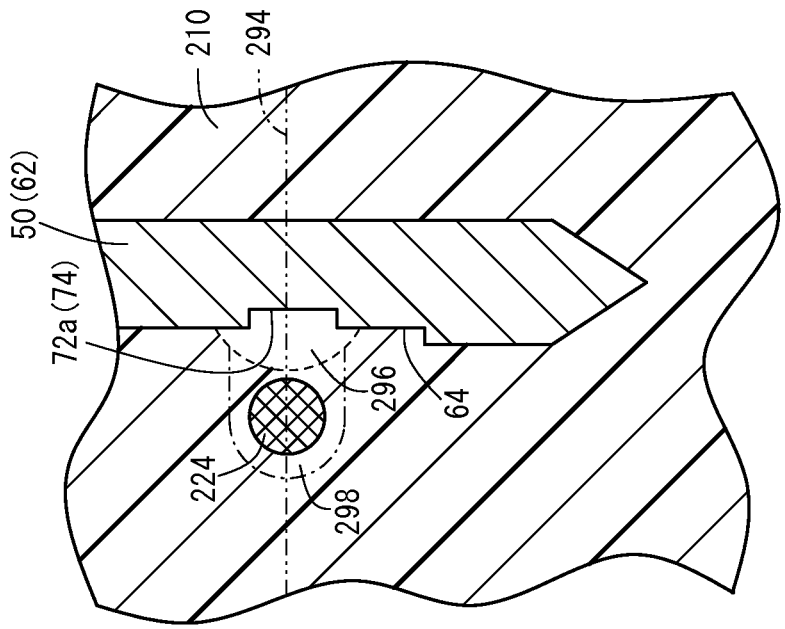
FIG. 15B is a fragmentary cross-sectional view showing an aspiration process according to an inventive example.
Figure 15A:
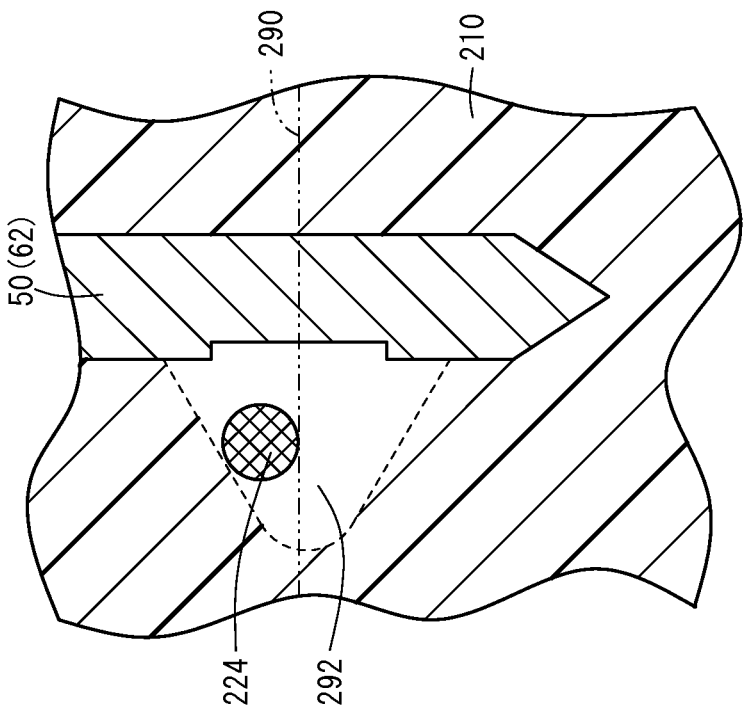
FIG. 15A is a fragmentary cross-sectional view showing an aspiration process according to a comparative example.

As shown in FIGS. 15A and 15B, it is assumed that the biopsy needle 10 is inserted in the breast 210 at a displaced position and thus the biopsy region 224 is positioned above a central axis 290 of the outer opening 64.

If the biopsy needle 10 is of a double-tube structure which is free of the inner tube 52 (see FIG. 3), but includes the outer tube 50 and the tube cutter 54, then it is necessary to increase the opening area of the outer opening 64 and increase the aspirating pressure of the aspirator 24 in order to extract the biopsy region 224 in its entirety without the need of re-insertion of the needle.

After the biopsy region 224 is extracted in its entirety by the biopsy needle 10, a cavity 292 having the peak at the central axis 290 is formed in the breast 210. In other words, the biopsy needle 10 aspirates and extracts not only the biopsy region 224, but also a wide region surrounding the biopsy region 224. As the biopsy needle 10 aspirates and extracts a large amount of tissue from the breast 210, it poses a large physical burden on the examinee 208.

As shown in FIG. 15B, in a case where the biopsy needle (i.e., a triple-tube structure which includes the outer tube 50, the inner tube 52, and the tube cutter 54) according to the present embodiment is used, the communication port 74 is moved to a position closest to the biopsy region 224. Then, the biopsy needle 10 extracts a first tissue sample, and as a result, a first cavity 296 (indicated by the broken line) is formed above the central axis 290 (indicated by the two-dot-and-dash line). The first cavity 296 lies between the communication port 74 and the biopsy region 224.

Subsequently, the biopsy needle 10 remains inserted in the breast 210, and, if necessary, the communication port 74 is positionally changed. Then, the biopsy needle 10 extracts a second tissue sample, and as a result, a second cavity 298 (indicated by the dot-and-dash line) is formed.

The first cavity 296 formed in the first tissue sampling process makes it easy to access the biopsy region 224. Owing thereto, the aspirating pressure for aspirating and extracting the biopsy region 224 can be lower than the aspirating pressure in the case as shown in FIG. 15A. It is therefore possible to minimize the amount of a tissue sample extracted from the breast 210. As can be seen from FIGS. 15A and 15B, the sum of the volumes of the first cavity 296 and the second cavity 298 is smaller than the volume of the cavity 292. Thus, the physical burden on the examinee 208 is reduced.

In step S13, the hand drive controller 264 moves the biopsy needle 10 toward the compression plate 222 after the biopsy needle 10 has extracted the biopsy region 224, thereby pulling the biopsy needle 10 out of the breast 210. Thereafter, the compression plate drive controller 266 moves the compression plate 222 upwardly to release the breast 210 from the compressed state.

The biopsy procedure is now ended. Since the outer tube 50 and the inner tube 52 jointly define only the single communication port 74, the biopsy needle 10 has only one aspirating range or sample extracting range for the biopsy region 224. Therefore, the biopsy needle 10 avoids the aspiration and extraction of living body regions other than the biopsy region 224 to be extracted, and hence minimizes the amount of a tissue sample extracted from the biopsy region 224.

The above embodiment may be modified according to first through fifth modifications described below. Those components of the first through fifth modifications which are identical to those of the biopsy needle 10, the sample extracting unit 12, and the mammographic apparatus 200 according to the above embodiment (see FIGS. 1 through 15B) are denoted by identical reference characters, and will not be described in detail below.

First Modification

In the above embodiment, the doctor refers to recommended values of aspirating conditions displayed on the display control panel 228, and, if necessary, operates the operating section 30 (see FIG. 1) and the operating switches (see FIG. 2) to change the setting values of the sample extracting unit 12 (see FIG. 13). On the other hand, according to a first modification, the mammographic apparatus may automatically set recommended values determined by the sample extracting unit 12a without the need for a manual setting process by the doctor.

Figure 16:
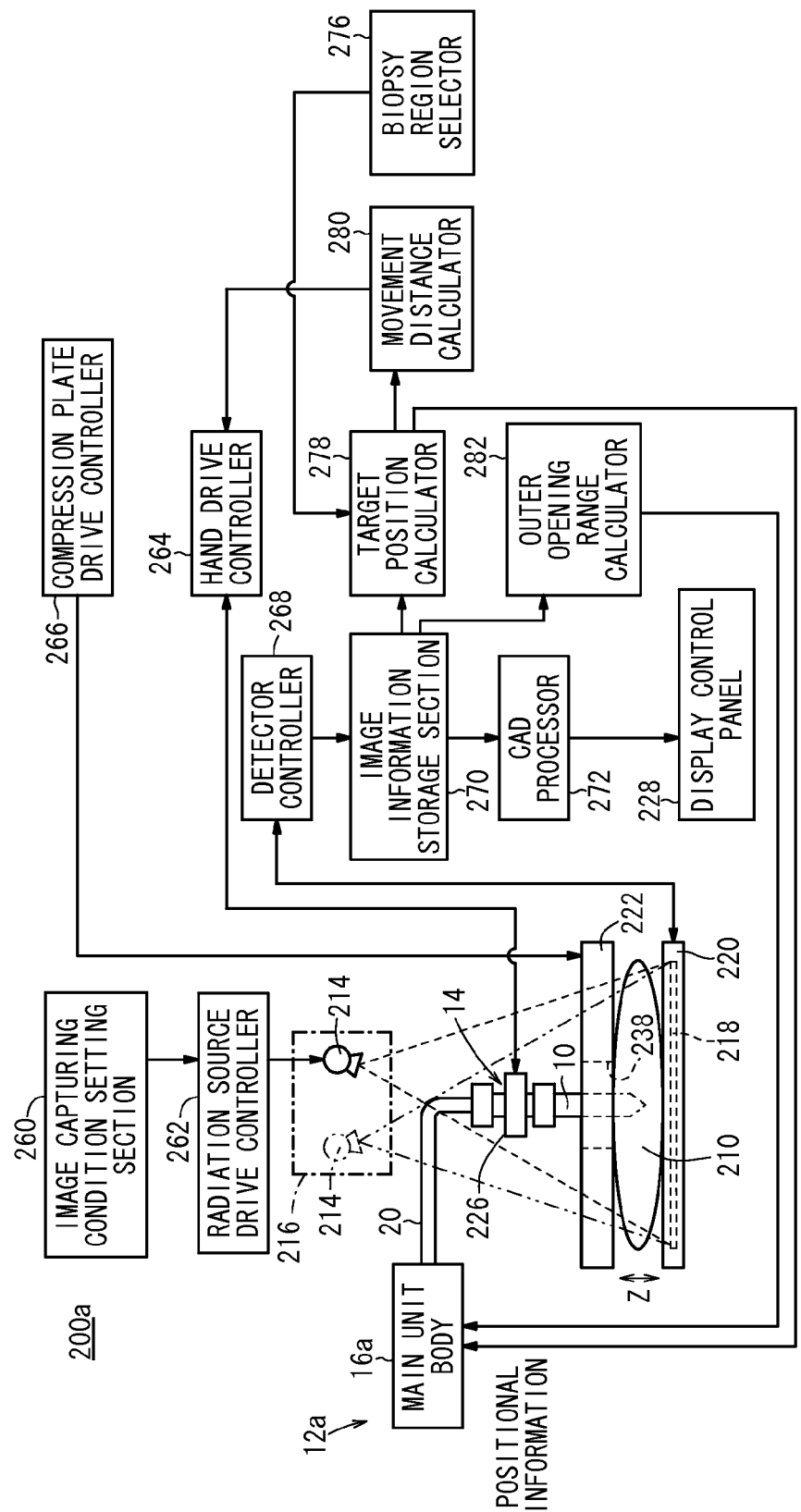
FIG. 16 is a block diagram of a control circuit of a mammographic apparatus according to a first modification.

FIG. 16 is a block diagram of a control circuit of a mammographic apparatus 200a according to the first modification. The control circuit of the mammographic apparatus 200a according to the first modification is different from the control circuit of the mammographic apparatus 200 according to the above embodiment in that the control circuit of the mammographic apparatus 200a is free of the aspirating condition determiner 284 and the opening information recorder 286 shown in FIG. 13. Data calculated by the target position calculator 278 and the outer opening range calculator 282 can be supplied to a main unit body 16a of a sample extracting unit 12a through a wired or wireless link.

Figure 17:
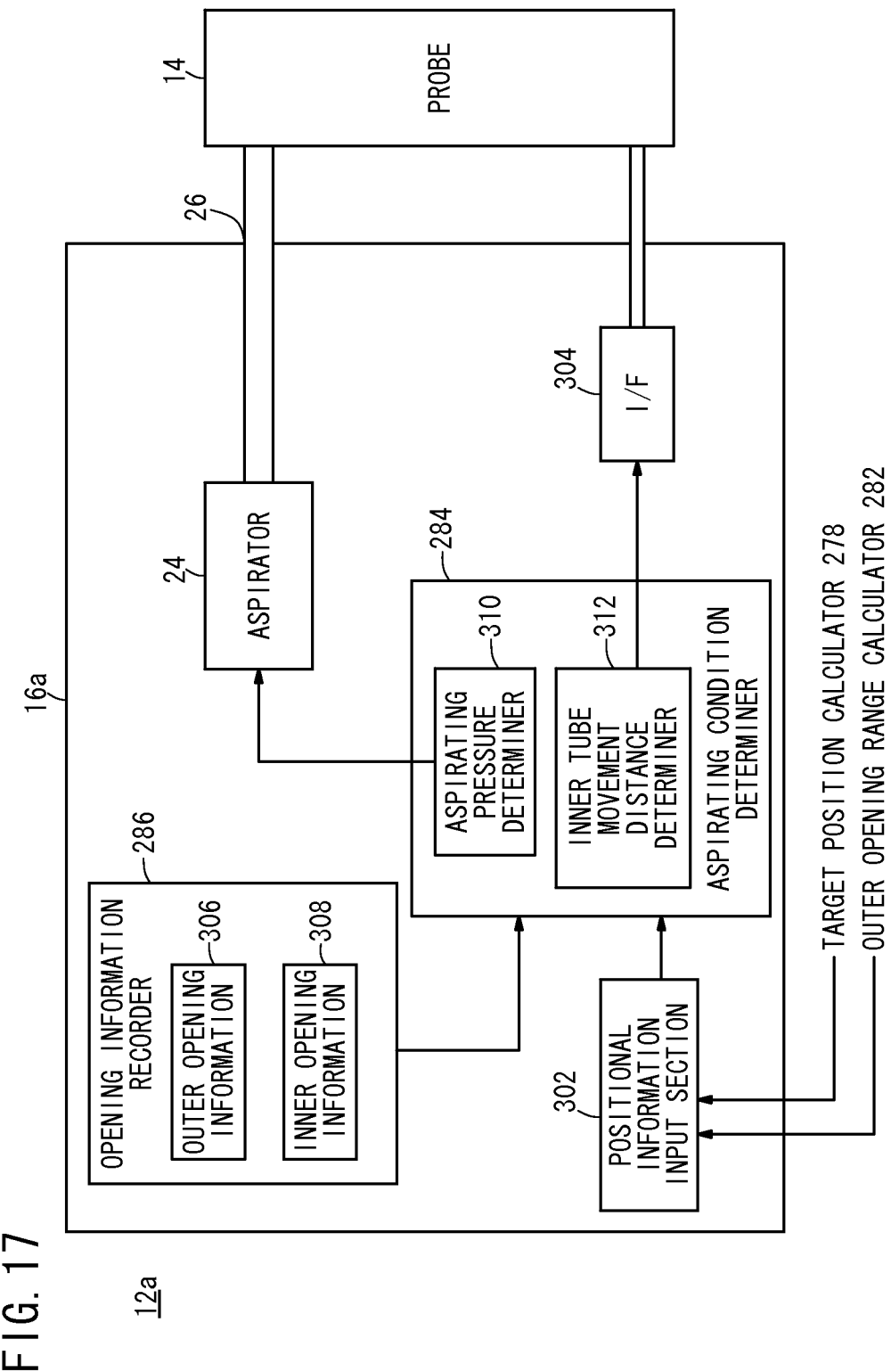
FIG. 17 is a block diagram of a control circuit of a sample extracting unit according to the first modification.

FIG. 17 is a block diagram of a control circuit of the main unit body 16a according to the first modification.

As shown in FIG. 17, the main unit body 16a includes a positional information input section 302, an opening information recorder 286, an aspirating condition determiner 284, an aspirator 24, and an I/F 304.

The main unit body 16a is electrically connected to the target position calculator 278 and the outer opening range calculator 282. The positional information input section 302 inputs the positional information from the target position calculator 278 and the outer opening range calculator 282.

The opening information recorder 286 records in advance outer opening information 306 about the number, position, and size of the outer opening 64 in the outer tube 50, and inner opening information 308 about the number, positions, and sizes of the inner openings 72a through 72c in the inner tube 52. The aspirating condition determiner 284 includes an aspirating pressure determiner 310 for determining an aspirating pressure for the aspirator 24, and an inner tube movement distance determiner 312 for determining a movement distance of the inner tube 52, i.e., a turning angle through which the inner tube 52 is turned and a displacement distance that the inner tube 52 is displaced in the Z'.

An operation sequence of the main unit body 16a shown in FIG. 17 will be described below. The operation sequence of the main unit body 16a includes steps which are identical to steps S1 through S6 and S10 through S13 (see FIG. 14). Those identical steps will not be described below.

The operation sequence of the main unit body 16a includes steps which are similar to, but different from, steps S7 through S9 as follows:

In the step corresponding to step S7, the positional information input section 302 inputs the positional information of the biopsy region 224 which is supplied from the target position calculator 278 and the positional information of the outer opening 64 which is supplied from the outer opening range calculator 282. If the doctor operates the mode switcher 36 (see FIG. 1) to switch to "AUAOMATIC" (automatic mode) in advance, then the above information is automatically input to the main unit body 16a.

Based on the positional information of the biopsy region 224 and the outer opening 64 that is input from the positional information input section 302, the aspirating pressure determiner 310 determines an aspirating pressure setting value for the aspirator 24 and sends the aspirating pressure setting value to the aspirator 24 in the step corresponding to step S8. The aspirator 24 aspirates the biopsy region 224 under an aspirating pressure according to the aspirating pressure setting value supplied thereto.

Based on the positional information of the biopsy region 224 and the outer opening 64 that is input from the positional information input section 302 and the outer opening information 306 and the inner opening information 308 that are recorded by the opening information recorder 286, the inner tube movement distance determiner 312 determines a setting value representative of a turning angle through which the inner tube 52 is turned and/or a displacement distance that the inner tube 52 is displaced in the Z'. The inner tube movement distance determiner 312 supplies the setting value to the probe 14 through the I/F 304 and the cable 20. The inner tube 52 is now moved to a position and attitude depending on the supplied setting value in the step corresponding to step S9.

As described above, it is highly convenient for the doctor if recommended values for aspirating conditions determined by the sample extracting unit 12a are automatically set without the need for a manual setting process by the doctor.

Second Modification

In the above embodiment, the inner openings 72a through 72c in the inner tube 52 have the same opening area. However, the inner openings 72a through 72c have different opening areas according to a second modification. The second modification will be described below with reference to FIG. 18. It is assumed that the inner tube 52 is angularly movable in the φ direction.

Figure 18:
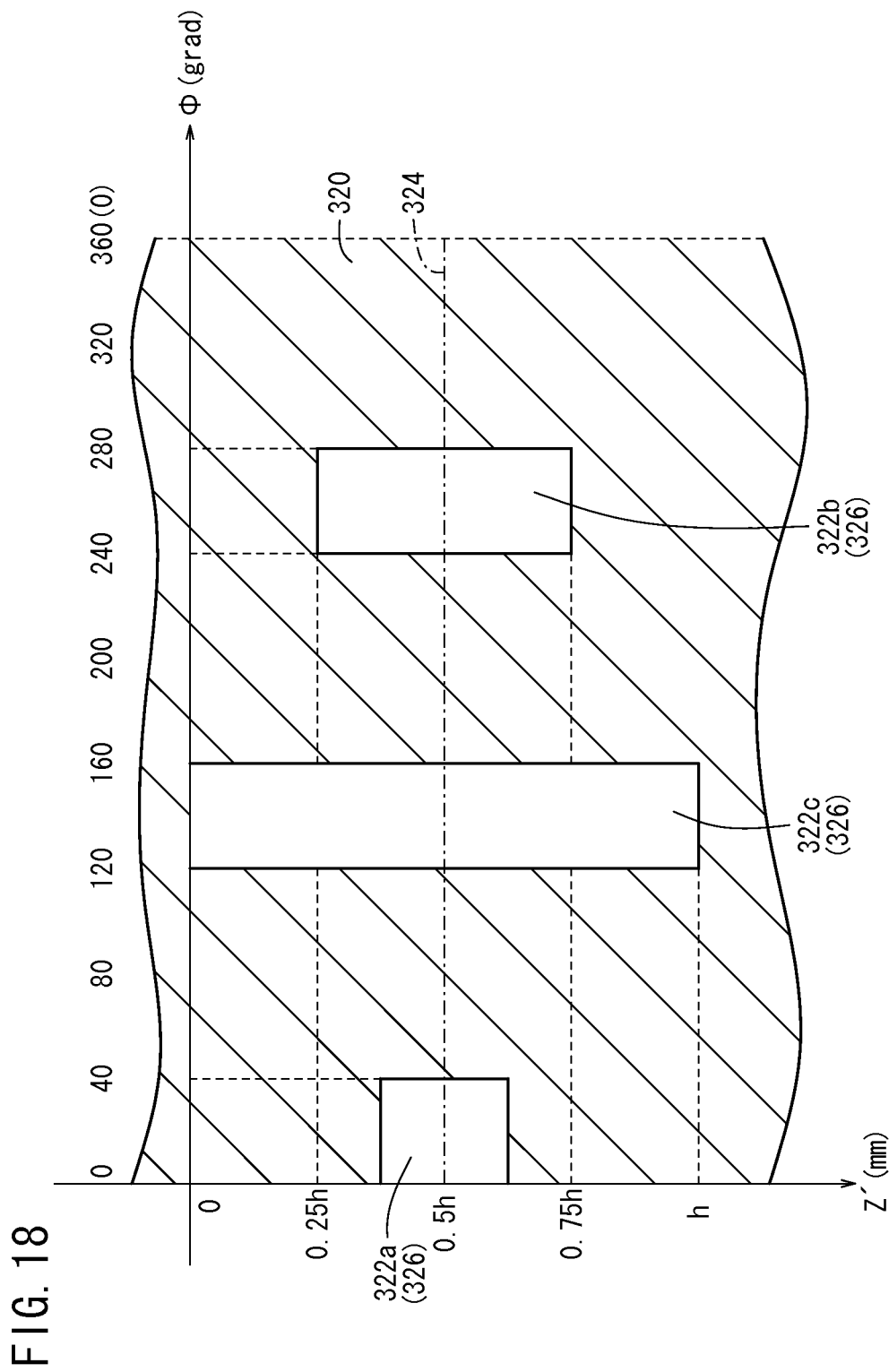
FIG. 18 is a fragmentary developed view of a side wall of an inner tube according to a second modification.

As shown in FIG. 18, the inner tube 52 has three inner openings 322a through 322c defined in a side wall 320 thereof. Each of the inner openings 322a through 322c has a length corresponding to 40 degrees in the φ direction. The inner openings 322a through 322c have different lengths 0.25 h, 0.5 h, and 1 h, respectively, in the Z' directions. The inner openings 322a through 322c have respective centers of gravity at positions (20 degrees, 0.5 h), (140 degrees, 0.5 h), and (260 degrees, 0.5 h), respectively.

In a state where the outer opening 64 (see FIG. 7A) and the inner opening 322a fully overlap each other (hereinafter referred to as "state 11"), a single rectangular communication port 326 is defined in a range represented by (0≤φ≤40) and (0.375 h≤Z'≤0.625 h).

In the case where only the inner tube 52 is turned through 120 degrees in the φ direction from the state 11, the state 11 changes to a state 12. In the state 12, the outer opening 64 and the inner opening 322b fully overlap each other, and a single rectangular communication port 326 is defined in a range represented by (240≤φ≤280) and (0.25 h≤Z'≤0.75 h).

In the case where only the inner tube 52 is further turned through 120 degrees in the φ direction from the state 12, the state 12 changes to a state 13. In the state 13, the outer opening 64 and the inner opening 322c fully overlap each other, and a single rectangular communication port 326 is defined in a range represented by (120≤φ≤160) and (0≤Z'≤h).

Since the three inner openings 322a through 322c have different opening areas and respective centers of gravity disposed on one circumferential line 324, the length of the communication port 326 in the Z' directions can be changed while the position of the peak of an aspirating pressure distribution (the vicinity of the circumferential line 324) being kept substantially in a given position. Therefore, the aspirating condition, i.e., the aspiratable range, can be set with increased freedom.

The three inner openings 322a through 322c may be arranged such that their centers of gravity are disposed on one tangential line parallel to the Z' directions. In such a case, the length of the communication port 326 in the φ direction can be changed while the position of the peak of an aspirating pressure distribution (the vicinity of the tangential line) being kept substantially in a given position.

Third Modification

In the above embodiment, the single outer opening 64 is defined in the side wall 70 of the outer tube 50. However, a plurality of outer openings may be defined in the side wall 70 of the outer tube 50 according to a third modification. The third modification will be described below with reference to FIG. 19. It is assumed that the inner tube 52 is movable back and forth in the Z' directions.

Figure 19:
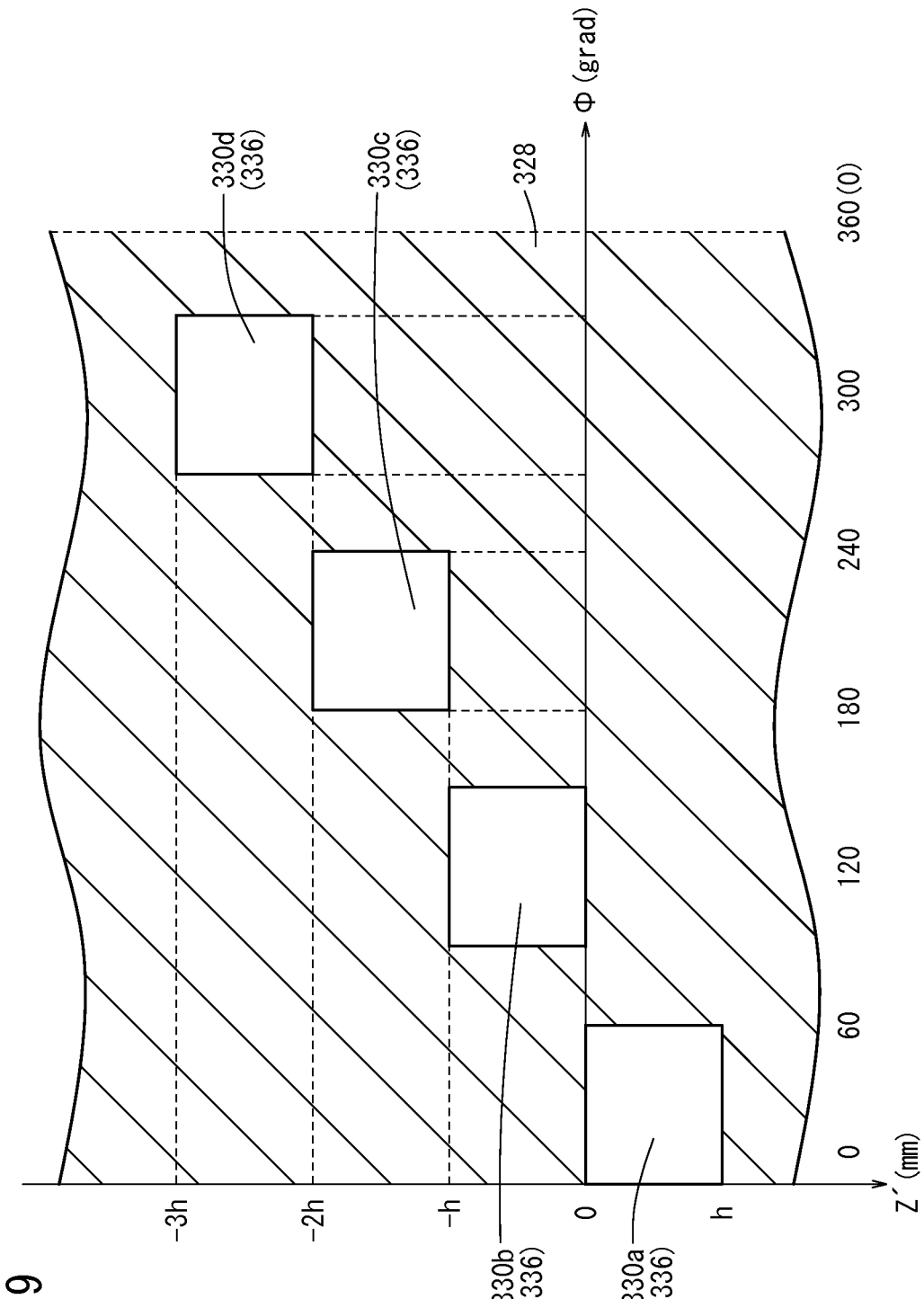
FIG. 19 is a fragmentary developed view of a side wall of an inner tube according to a third modification.

As shown in FIG. 19, the inner tube 52 has four inner openings 330a through 330d defined in a side wall 328 thereof. Each of the inner openings 330a through 330d is of a rectangular shape which has a length h in the Z' directions and a length represented by 60 degrees in the φ direction. The inner openings 330a through 330d have respective opening areas which are identical to each other.

The inner openings 330a through 330d are spaced at equal intervals h along the Z'2 direction and also spaced at equal intervals represented by 90 degrees along the φ direction.

Figure 20:
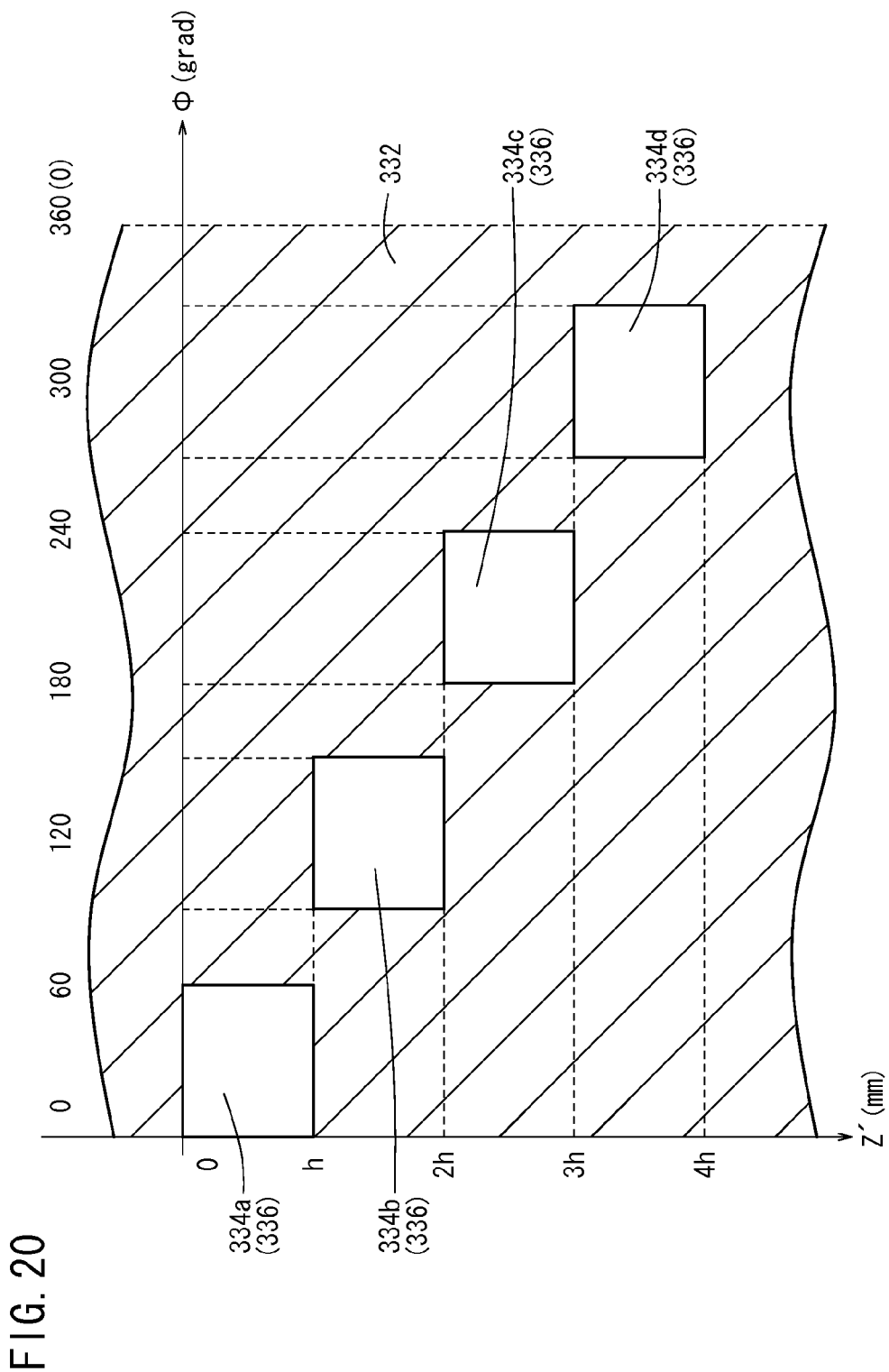
FIG. 20 is a fragmentary developed view of a side wall of an outer tube according to the third modification.

As shown in FIG. 20, the outer tube 50 has four outer openings 334a through 334d defined in a side wall 332 thereof. Each of the outer openings 334a through 334d is of a rectangular shape which has a length h in the Z' directions and a length represented by 60 degrees in the φ direction. The outer openings 334a through 334d have the same opening areas. Therefore, the areas of the outer openings 334a through 334d are equal to the areas of the inner openings 330a through 330d.

The outer openings 334a through 334d are spaced at equal intervals h along the Z'1 direction and also spaced at equal intervals represented by 90 degrees along the φ direction.

In a state where the outer opening 334a and the inner opening 330a fully overlap each other (hereinafter referred to as as "state 21"), a single rectangular communication port 336 is defined in a range represented by (0≤φ≤60) and (0≤Z'≤1 h). Since the other inner openings 330b through 330d fully overlap the side wall 332 of the outer tube 50, no communication port 336 is defined in the positions of the inner openings 330b through 330d. Also, since the other outer openings 334b through 334d fully overlap the side wall 328 of the inner tube 52, no communication port 336 is defined in the positions of the outer openings 334b through 334d.

In the case where only the inner tube 52 is moved a distance h in the Z'1 direction from the state 21, the state 21 changes to a state 22. In the state 22, the outer opening 334b and the inner opening 330b fully overlap each other, and a single rectangular communication port 336 is defined in a range represented by (90≤φ≤150) and (h≤Z'≤2 h).

In the case where only the inner tube 52 is further moved a distance h in the Z'1 direction from the state 22, the state 22 changes to a state 23. In the state 23, the outer opening 334c and the inner opening 330c fully overlap each other, and a single rectangular communication port 336 is defined in a range represented by (180≤φ≤240) and (2 h≤Z'≤3 h).

In the case where only the inner tube 52 is further moved a distance h in the Z'1 direction from the state 23, the state 23 changes to a state 24. In the state 24, the outer opening 334d and the inner opening 330d fully overlap each other, and a single rectangular communication port 336 is defined in a range represented by (270≤φ≤330) and (3 h≤Z'≤4 h).

The third modification, with the plural outer openings 334a through 334d defined in the side wall 332 of the outer tube 50, offers the same advantages as those of the above embodiment.

Fourth Modification

In the above embodiment, the rectangular outer opening 64 is defined in the side wall 70 of the outer tube 50 (see FIG. 7A). However, an outer opening having any of various shapes may be defined in the side wall 70 of the outer tube 50 according to a fourth modification. The fourth modification will be described below with reference to FIG. 21.

Figure 21:
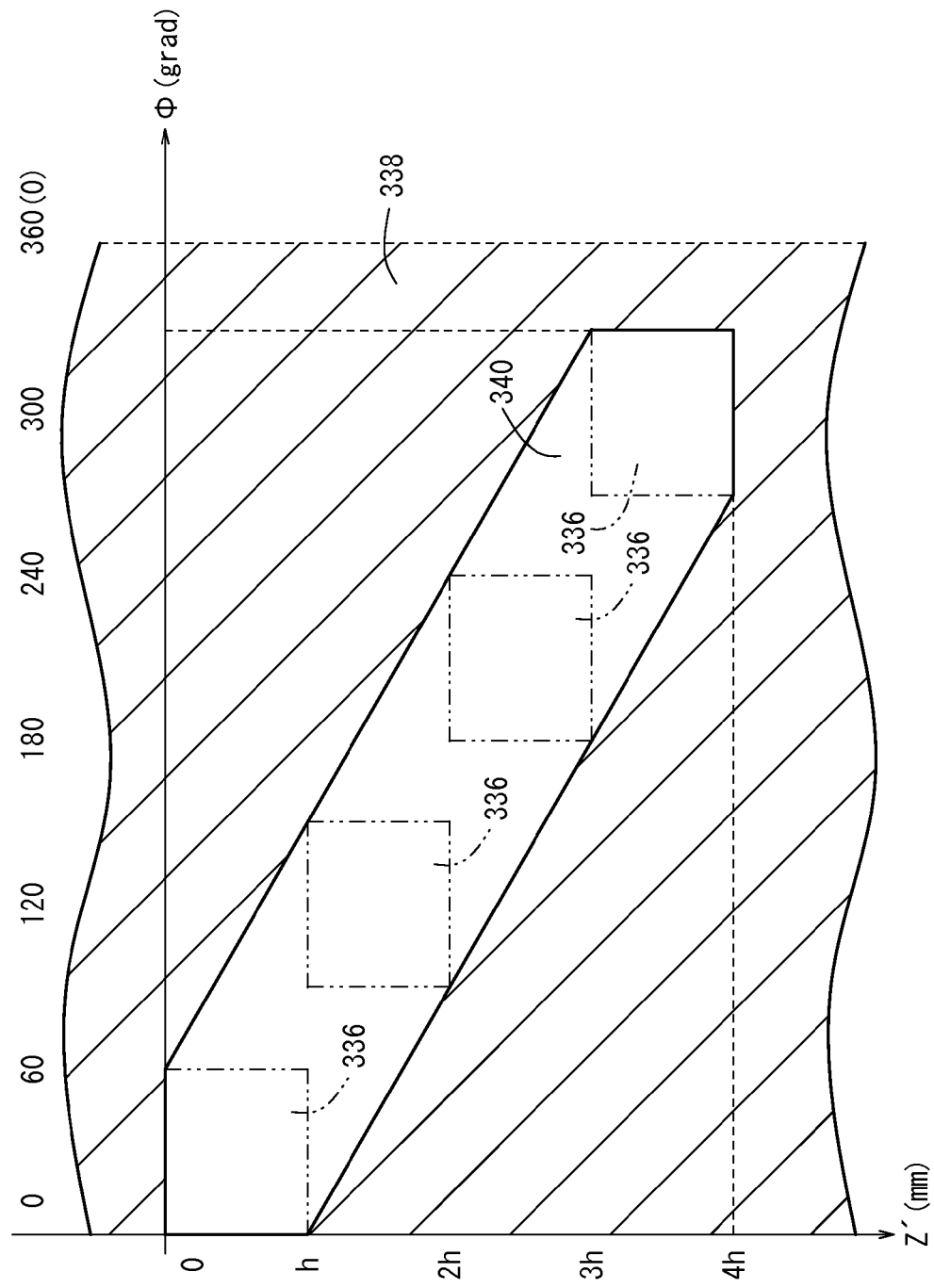
FIG. 21 is a fragmentary developed view of a side wall of an outer tube according to a fourth modification.

As shown in FIG. 21, the outer tube 50 has a single outer opening 340 which is of a hexagonal shape including a pair of elongate opposite sides, defined in a side wall 338 thereof. The elongate opposite sides correspond to straight lines interconnecting lower left vertexes and upper right vertexes of the outer openings 334a through 334d shown in FIG. 20. Thus, the outer opening 340 cover all the outer openings 334a through 334d shown in FIG. 20.

As with the third modification shown in FIG. 19, the inner tube 52 has four inner openings 330a through 330d defined in the side wall 328 thereof, and the inner tube 52 is movable back and forth in the Z' directions.

As with the third modification, the inner tube 52 is moved a predetermined distance in the Z' directions, whereby a single rectangular communication port 336 is selectively defined.

Fifth Modification

In the above embodiment and the third and fourth modifications, the inner tube 52 is selectively movable, i.e., angularly movable or axially movable back and fourth. However, the inner tube 52 may be both angularly movable and axially movable back and fourth. For example, a biopsy needle 10 may include the outer tube 50 (see FIG. 7A) according to the above embodiment and the inner tube 52 (see FIG. 19) according to the third modification. In this case, the inner tube 52 may be moved to cause the outer opening 64 and the inner opening 330a (or either one of the inner openings 330b through 330d) to selectively overlap each other.

The numbers of the outer opening 64 and the inner openings 72a through 72c are not limited to the numbers according to the above embodiment and modifications thereof. Also, the communication port 74 may be of any of various shapes including a circular shape, a polygonal shape, etc. in addition to the rectangular shape.

Although certain preferred embodiments of the present invention have been shown and described in detail, it should be understood that various changes and modifications may be made therein without departing from the scope of the appended claims.

What is claimed is:

1. A biopsy needle comprising:
    an outer tube having a hollow cylindrical shape; and
    an inner tube having a hollow cylindrical shape and which is movably disposed within the outer tube for movement in an axial direction or a circumferential direction;
    wherein the inner tube has a plurality of inner openings defined in a side wall thereof; and
        the outer tube has a single outer opening defined in a side wall thereof, an opening area of the outer opening being greater than an opening area of each of the inner openings, and in response to movement of the inner tube, the outer opening selectively overlaps one of the plurality of inner openings thereby to define a communication port which communicates with an interior of the inner tube.

2. The biopsy needle according to claim 1, wherein the inner openings are disposed so as not to overlap each other in the axial direction of the inner tube.

3. The biopsy needle according to claim 1, wherein the inner openings are disposed in respective positions which are different from each other in the axial direction of the inner tube.

4. The biopsy needle according to claim 1, wherein the inner openings have respective opening areas which are different from each other and have respective centers of gravity disposed on one circumferential line.

5. The biopsy needle according to claim 1, wherein the inner openings have respective opening areas which are identical to each other.

6. A sample extracting unit comprising:
    a biopsy needle according to claim 1; and
    an aspirating mechanism for aspirating a mass which is disposed near the communication port defined by the outer tube and the inner tube, into the inner tube.

7. The sample extracting unit according to claim 6, wherein the aspirating mechanism has a changeable aspirating pressure.

8. The sample extracting unit according to claim 7, further comprising:
    a positional information input section for inputting positional information of the biopsy needle and the mass; and
    an aspirating pressure determiner for determining the aspirating pressure for the aspirating mechanism based on the positional information input by the positional information input section.

9. The sample extracting unit according to claim 8, further comprising:
    an opening information recorder for recording opening information about the outer opening and the inner openings; and
    an inner tube movement distance determiner for determining a movement distance of the inner tube based on the positional information input by the positional information input section and the opening information recorded by the opening information recorder.

10. A biopsy apparatus comprising:
a sample extracting unit according to claim 6;
a radiation source for applying a radiation to an object to be examined of a subject;
a radiation detector for detecting the radiation which has passed through the object and converting the detected radiation into a radiographic image; and
a position calculator for calculating a three-dimensional position of a biopsy region in the object based on two radiographic images which are generated by the radiation detector in an image capturing process which is performed by applying the radiation from at least two angular positions to the object with the radiation source.

11. The biopsy needle according to claim 1, wherein the outer opening is of a rectangular shape which is elongate in the axial direction.

12. A biopsy needle comprising:
an outer tube having a hollow cylindrical shape; and
an inner tube having a hollow cylindrical shape and which is movably disposed within the outer tube for movement in an axial direction or a circumferential direction;
wherein the inner tube has a plurality of inner openings defined in a side wall thereof;
the outer tube has at least one outer opening defined in a side wall thereof, an opening area of the at least one outer opening being greater than an opening area of each of the inner openings, and in response to movement of the inner tube, the at least one outer opening selectively overlaps one of the plurality of inner openings thereby to define a communication port which communicates with an interior of the inner tube; and
a circumferential length of the outer opening is greater than a circumferential length of each of the inner openings, and/or an axial length of the outer opening is greater than an axial length of each of the inner openings.

13. The biopsy needle according to claim 12, wherein the inner openings are disposed in respective positions which are different from each other in the axial direction of the inner tube.

14. A biopsy needle comprising:
an outer tube having a hollow cylindrical shape;
an inner tube having a hollow cylindrical shape and which is movably disposed within the outer tube for movement in an axial direction or a circumferential direction; and
a tube cutter movable in the axial direction and having a cutting face on a distal end;
wherein the inner tube has a plurality of inner openings defined in a side wall thereof; and the outer tube has at least one outer opening defined in a side wall thereof, an opening area of the at least one outer opening being greater than an opening area of each of the inner openings, and in response to movement of the inner tube, the at least one outer opening selectively overlaps one of the plurality of inner openings thereby to define a communication port which communicates with an interior of the inner tube.

* * * * *